(12) United States Patent
Lin et al.

(10) Patent No.: US 9,453,219 B2
(45) Date of Patent: Sep. 27, 2016

(54) COSMETIC DESIGNS AND PRODUCTS USING INTRONIC RNA

(75) Inventors: Shi-Lung Lin, Arcadia, CA (US); David TS Wu, Taipei (TW)

(73) Assignee: MELLO BIOTECH TAIWAN CO., LTD., Taipei (TW)

( * ) Notice: Subject to any disclaimer, the term of this patent is extended or adjusted under 35 U.S.C. 154(b) by 1360 days.

(21) Appl. No.: 12/003,662

(22) Filed: Dec. 28, 2007

(65) Prior Publication Data

US 2009/0170204 A1 Jul. 2, 2009

Related U.S. Application Data

(63) Continuation-in-part of application No. 10/439,262, filed on May 15, 2003, now abandoned, and a continuation-in-part of application No. 11/278,143, filed on Mar. 31, 2006, now abandoned.

(60) Provisional application No. 61/000,797, filed on Oct. 29, 2007.

(51) Int. Cl.
*C12N 15/113* (2010.01)
*C12N 15/11* (2006.01)

(52) U.S. Cl.
CPC ........... *C12N 15/111* (2013.01); *C12N 15/113* (2013.01); *C12N 2310/111* (2013.01); *C12N 2310/141* (2013.01); *C12N 2320/30* (2013.01); *C12N 2320/50* (2013.01)

(58) Field of Classification Search
CPC .......................... C12N 15/113; C12N 15/1137
USPC ....... 435/6, 91.1, 91.31, 320.1, 455; 514/44; 536/23.1, 24.1, 24.5
See application file for complete search history.

(56) References Cited

U.S. PATENT DOCUMENTS

| | | | |
|---|---|---|---|
| 4,289,850 A | 9/1981 | Robinson et al. | |
| 6,159,714 A | 12/2000 | Usman et al. | |
| 6,514,506 B1 | 2/2003 | Mammone et al. | |
| 6,521,267 B1 | 2/2003 | Steck et al. | |
| 6,649,150 B2 | 11/2003 | Chaudhuri et al. | |
| 6,710,076 B2 | 3/2004 | Ancira | |
| 6,838,481 B1 | 1/2005 | Kim et al. | |
| 6,852,699 B1 | 2/2005 | Schonrock et al. | |
| 6,969,509 B2 | 11/2005 | Chaudhuri et al. | |
| 6,994,874 B2 | 2/2006 | Leverett et al. | |
| 6,998,130 B2 | 2/2006 | Wortzman et al. | |
| 7,019,029 B2 | 3/2006 | Perricone | |
| 7,025,957 B2 | 4/2006 | Arquette | |
| 7,025,977 B2 | 4/2006 | Wortzman et al. | |
| 7,029,709 B2 | 4/2006 | Arquette | |
| 7,060,304 B2 | 6/2006 | Leverett et al. | |
| 7,097,866 B2 | 8/2006 | Arquette | |
| 7,105,184 B2 | 9/2006 | Pauly et al. | |
| 7,125,572 B2 | 10/2006 | Lee | |
| 7,192,617 B2 | 3/2007 | Nagamine et al. | |
| 7,247,321 B2 | 7/2007 | Leverett et al. | |
| 7,250,157 B2 | 7/2007 | Brown et al. | |
| 7,268,108 B2 | 9/2007 | Pinel | |
| 2004/0215006 A1* | 10/2004 | Bennett et al. | 536/23.1 |
| 2005/0059005 A1* | 3/2005 | Tuschl et al. | 435/6 |
| 2006/0003322 A1* | 1/2006 | Bentwich | 435/6 |
| 2006/0228800 A1 | 10/2006 | Lin et al. | |

FOREIGN PATENT DOCUMENTS

| | | | |
|---|---|---|---|
| JP | 2004-115466 A | | 4/2004 |
| JP | 2006-342107 A | | 12/2006 |
| JP | 2007-119384 A | | 5/2007 |
| WO | WO 01/79223 | * | 4/2001 |
| WO | WO 02/024899 | * | 7/2002 |
| WO | WO 2004/024940 | * | 3/2004 |

OTHER PUBLICATIONS

Fire et al. (1998) Potent and specific genetic interference by double-stranded RNA in Caenorhabditis elegans. *Nature* 391: 806-811.
Elbashir et.al. (2001) Duplexes of 21-nucleotide RNAs mediate RNA interference in cultured mammalian cells. *Nature* 411: 494-498.
Lin et.al. (2001) A Novel mRNA-cDNA interference phenomenon for silencing bcl-2 expression in human LNCaP cells. *Biochem. Biophys. Res. Commun.* 281: 639-644.
Grant S.R. (1999) Dissecting the mechanisms of posttranscriptional gene silencing: divide and conquer. *Cell* 96: 303-306.
Lin et.al. (2001) D-RNAi (messenger RNA-antisense DNA interference) as a novel defense system against cancer and viral infections. *Current Cancer Drug Targets* 1: 241-247.
Bartel D.P. (2004) MicroRNAs: genomics, biogenesis, mechanism, and function. *Cell* 116: 281-297.
Lin et.al. (2004a) Novel RNAi therapy—Intron-derived microRNA drugs. *Drug Design Reviews* 1: 247-255.
Stark et.al. (1998) How cells respond to interferons. *Annu. Rev. Biochem.* 67: 227-264.
Brantl S. (2002) Antisense-RNA regulation and RNA interference. *Biochimica et Biophysica Acta* 1575: 15-25.
Jen et.al. (2000) *Stem Cells* 18: 307-319.
Ying et.al. (1999) Suppression of activin-induced apoptosis by novel antisense strategy in human prostate cancer cells. *Biochem. Biophys. Res. Commun.* 265: 669-673.

(Continued)

*Primary Examiner* — J. E. Angell
(74) *Attorney, Agent, or Firm* — Birch, Stewart, Kolasch & Birch, LLP

(57) ABSTRACT

The present invention relates to a method and composition for generating a non-naturally occurring intron and its components capable of being processed into small hairpin RNA (shRNA) and/or microRNA (miRNA) molecules by skin cells and thus inducing specific gene silencing effects on skin pigment-related genes and/or aging-causing genes in the cells. The gene silencing effects so obtained are not only useful for lightening and whitening skin colors but also useful for suppressing unwanted aging gene activities in skins.

11 Claims, 8 Drawing Sheets
(5 of 8 Drawing Sheet(s) Filed in Color)

(56) References Cited

OTHER PUBLICATIONS

Tuschl T. (2002) Expanding small RNA interference. *Nat Biotechnol.* 20: 446-448.

Miyagishi M, Taira K. (2002) U6 promoter-driven siRNAs with four uridine 3' overhangs efficiently suppress targeted gene expression in mammalian cell. *Nat Biotechnol* 20: 497-500.

Lee NS, et al. (2002) Expression of small interfering RNAs targeted agains HIV-1 rev transcripts in human cells. *Nat Biotechnoly* 20: 500-505.

Paul C.P. et al. (2002) Effective expression of small interfering RNA in human cells. *Nat. Biotechnology* 20:505-508.

Gunnery S, Ma Y, Mathews MB. (1999) Termination sequence requirements vary amoung genes transcribed by RNA polymerase III. *J Mol Biol.* 286: 745-757.

Schramm L, Hernandez N. (2002) Recruitment of RNA polymerase III to its target promoters *Genes Dev.* 16: 2593-2620.

Sledz, CA, Holko M, de Veer MJ, Silverman RH, Williams BR. (2003) Activation of the interferon system by short-interfering RNAs. *Nat Cell Biol.* 5: 834-839.

Grimm D, Streetz KL, Jopling CL, Storm TA, Pandey K, Davis CR, Marion P, Salazar F, Kay MA. (2006) Fatality in mice due to oversaturation of cellular microRNA/short hairpin RNA pathways. *Nature* 441: 537-541.

Nott et.al. (2003) *RNA* 9: 607-617.

Clement et.al. (1999) *RNA* 5: 206-220.

Lin SL, Chang D. Wu DY, Ying SY. (2003) A novel RNA splicing-mediated gene silencing mechanism potential for genome evolution. *Biochem Biophys Res Commun.* 310: 754-760.

Lin et.al. (2005) Asymmetry of intronic pre-microRNA structures in functional RISC assembly. *Gene* 356: 32-38.

Ying et.al. 2004 Intron-derived microRNAs—fine tuning of gene functions. *Gene* 342: 25-28.

Ying et.al. (2005) Intronic microRNAs. *Biochem Biophys Res Commun.* 326: 515-520.

Zhang G., Taneja KL, Singer RH, Green MR. (1994) Localization of pre-mRNA splicing in mammalian nuclei. *Nature* 372: 809-812.

Lewis BP, Green RE, Brenner SE. (2003) Evidence for the widespread coupling of alternative splicing and nonsense-mediate mRNA decay in humans. *Proc. Natl. Acad. Sci. USA* 100: 189-192.

Ghosh S. Garcia-Blanco MA. (2000) Coupled in vitro synthesis and splicing of RNA polymerase II transcripts. *RNA* 6: 1325-1334.

Tang, G. (2005) *Trends Biochem Sci.* 30: 106-114.

Lin et al. (2008) Intron-mediated RNA interference and microRNA (miRNA). *Frontiers in Bioscience* 13: 2216-2230.

Lin SL, Ying SY. (2006a) Gene silencing in vitro and in vivo using intronic microRNAs. *Methods Mol Biol.* 342: 295-312.

Lin SL, Chang SJE, Ying SY. (2006b) Transgene-like animal model using intronic microRNAs. *Methods Mol Biol.* 342: 321-334.

Lee Y, Ahn C, Han J, Choi H, Kim J, Yim J, Lee J, Provost P, Radmark O, Kim S, Kim VN. (2003). The nuclear RNase III Drosha initiates microRNA processing. *Nature* 425: 415-419.

Lewin B. (2000) *Genes*, Seventh Edition, Oxford University press, p. 688-690.

Holen et.al. (2002) *Nucleic Acid Res.* 30: 1757-1766.

Krol et.al. (2004) *J. Biol. Chem.* 279: 42230-42239.

Rose A.B. (2002) *RNA* 8: 1444-1451.

Jin et al. (2004) *Nat Cell Biol.* 6: 1048-1053.

Database DDBJ/EMBL/GenBank[online], Accession No. AY101192, <http://www.ncbi.nlm.nih.gov/nuccore/AY101192>, Jun. 15, 2002 uploaded, Definition: *Homo sapiens* CD44 antigen (CD44) mRNA, complete cds.

Database DDBJ/EMBL/GenBank[online], Accession No. NM_000372, <http://www.ncbi.nlm.nih.gov/nuccore/113722118?sat=OLD06&satkey=9622881>, Jul. 30, 2007 uploaded, Definition: *Homo sapiens* tyrosinase (oculocutaneous albinism IA)(TYR), mRNA.

Database DDBJ/EMBL/GenBank[online], Accession No. NM_007312, <http://www.ncbi.nlm.nih.gov/nuccore/24497560?sat=OLD06&satkey=9796841>, Jul. 1, 2007 uploaded, Definition: *Homo sapiens* hyaluronoglucosaminidase 1 (HYAL1), transcript variant1, mRNA.

Database DDBJ/EMBL/GenBank[online], Accession No. NM_012485, <http://www.ncbi.nlm.nih.gov/nuccore/7108350?sat=OLD06&satkey+9603765>, Jul. 30, 2007 uploaded, Definition: *Homo sapiens* hyaluronan-mediated motility receptor (RHAMM)(HMMR), transcript variant 2, mRNA.

Du, G. et al, "Design of expression vectors for RNA interference based on miRNAs and RNA splicing," *FEBS Journal*, 2006, vol. 273, pp. 5421-5427.

* cited by examiner

B

Microarray analysis – miR–/miR-Tyr

| Gene | Accession # | change |
|---|---|---|
| tyosinase | NM000372 | −1.3 |
| tyosinase-associated protein 1 (TRP1) | NM000550 | −0.6 |
| endothelin 2 (ET2) | NM001956 | −0.3 |
| proliferating cell nuclear antigen (PCNA) | NM182649 | −0.3 |
| hUpf 1 | NM002911 | +0.3 |
| decapping protein (DCP2) | NM152624 | +0.3 |
| ribonuclease XRN 1 | NM019001 | +0.4 |

C

COSMETIC DESIGNS AND PRODUCTS USING INTRONIC RNA

The present application claims priority to the U.S. Provisional Patent Application No. 61/000,797 filed on Oct. 31, 2007, entitled "Novel Cosmetic Designs and Products Using Intronic RNA" by the inventors Shi-Lung Lin and David Wu. The present application also claims the benefit of the U.S. patent application Ser. No. 10/439,262 filed on May 15, 2003, entitled "RNA-Splicing and Processing-Directed Gene Silencing and the Relative Applications Thereof", and No. 11/278,143 filed on Mar. 31, 2006, entitled "Novel Transgenic Methods Using Intronic RNA", which are hereby incorporated by reference as if fully set forth herein. Furthermore, the present application is a continuation-in-part application of U.S. patent application Ser. Nos. 10/439,262 and 11/278,143.

FIELD OF THE INVENTION

This invention relates generally to a means for development and generation of cosmetic products for skin care. More particularly, the present invention relates to a method and composition for generating a non-naturally occurring intron and its components capable of being processed into small hairpin RNA (shRNA) and/or microRNA (miRNA) molecules by skin cells and thus inducing specific gene silencing effects on skin pigment-related genes and/or aging-causing genes in the cells. The gene silencing effects so obtained are not only useful for lightening and whitening skin colors but also useful for suppressing unwanted aging gene activities in skins.

BACKGROUND OF THE INVENTION

Prevention of hyperpigmentation (i.e. sun-burn) and aging is the key means for having healthy skins. However, many of the skin pigmentation and aging processes are associated with personal gene activities. For example, tyrosinase (Tyr), a melanocytic membrane-bound glycoprotein, is the rate-limiting enzyme critical for melanin (black pigment) biosynthesis in skins and hairs, while hyaluronidase (Hyal) often causes skin wrinkle by degrading subcutaneous hyaluronan (HA), the major anti-aging extracellular matrix in skins. Therefore, a good skin care can be achieved by suppressing these unwanted gene activities.

Currently, there is no prior art related to hyaluronidase inhibitor for wrinkle removal. For skin whitening and lightening, many prior arts attempting to inhibit tyrosinase function often use hormone-derived inhibitory peptides, small molecular chemicals and some plant extracts, including oligopeptides (e.g. U.S. Pat. No. 7,268,108 to Pinel; U.S. Pat. No. 6,852,699 to Schonrock), hydroxytetronic acid derivatives (e.g. U.S. Pat. No. 7,019,029 to Perricone), benzoyl compounds (e.g. U.S. Pat. No. 6,838,481 to Kim), hydroquinone compositions (e.g. U.S. Pat. Nos. 6,998,130 and 7,025,977 to Wortzman), alcohol diol and triol analogues (e.g. U.S. Pat. No. 7,250,157 to Brown), kojic acid derivatives (e.g. U.S. Pat. No. 6,710,076 to Ancira), ascomycete-derived enzymes (e.g. U.S. Pat. No. 6,514,506 to Mammone), and plant extracts (e.g. U.S. Pat. No. 7,192,617 to Nagamine; U.S. Pat. No. 7,125,572 to Lee; U.S. Pat. No. 6,521,267 to Steck; U.S. Pat. No. 7,105,184 to Pauly; U.S. Pat. Nos. 6,994,874, 7,060,304, and 7,247,321 to Leverett; U.S. Pat. Nos. 7,025,957, 7,029,709, and 7,097,866 to Arquette; U.S. Pat. Nos. 6,649,150 and 6,969,509 to Chaudhuri). Although these materials and methods may work well in vitro, only a few of them, such as hydroquinone and its derivatives, are able to induce good hypopigmenting effects in clinical trials (Solano et.al. (2006) *Pigment Cell Res.* 19: 550-571). Nevertheless, all hydroquinone derivatives leading to a reactive quinone are putative cytotoxic agents. The gap between in-vitro and in-vivo studies suggests that innovative strategies are needed for validating their safety and efficacy. (These publications and all other cited publications and patents in this application are hereby incorporated by reference as if fully set forth herein.)

With the advance of recent RNA interference (RNAi) technologies, novel small RNA agents have been found to provide more potent effects in targeted gene suppression, including the utilization of double-stranded short interfering RNA (e.g. dsRNA/siRNA) (Fire et al. (1998) *Nature* 391: 806-811; Elbashir et al. (2001) *Nature* 411: 494-498) and doxyribonucleotidylated-RNA interfering molecules (e.g. D-RNAi) (Lin et al. (2001) *Biochem. Biophys. Res. Commun.* 281: 639-644). Conceivably, these small RNA agents may be used to develop new cosmetic designs and products for skin care. In principle, the RNAi mechanism elicits a post-transcriptional gene silencing (PTGS) phenomenon capable of inhibiting specific gene function with high potency at a few nanomolar dosage, which has been proven to have lasting effect and much less toxic than conventional gene-knockout methods using antisense oligonucleotides or small molecule chemical inhibitors (Lin et al. (2001) *Current Cancer Drug Targets* 1: 241-247). As reported in many previous studies (Grant, S. R. (1999) *Cell* 96: 303-306; Elbashir et al. (2001) supra; Lin et al. (2001) supra; Lin et al. (2004a) *Drug Design Reviews* 1: 247-255), the siRNA-induced gene silencing effects may last over one week, while the D-RNAi effects can even sustain up to one month after one treatment. The siRNA/D-RNAi agents evoke a series of intracellular sequence-specific mRNA degradation and/or translational suppression processes, affecting all highly homologous gene transcripts, namely co-suppression. It has been observed that such co-suppression results from the generation of small RNA products (21-25 nucleotide bases) by the enzymatic activities of RNaseIII endoribonucleases (Dicer) and/or RNA-directed RNA polymerases (RdRp) on aberrant RNA templates, which are usually the derivatives of foreign transgenes or viral genomes (Grant, S. R. (1999) supra; Elbashir et al. (2001) supra; Lin et al. (2001) supra). Based on this well-established RNAi mechanism, prior arts attempting to inhibit tyrosinase function using synthetic siRNA and/or dsRNA agents include U.S. Pat. Application Publication No. 20050137151 to Binetti and U.S. Pat. Application Publication No. 20070134188 to Collin-Djangone.

Although the modern RNAi technologies may offer a new avenue for suppressing unwanted gene function in skins, the applications thereof have not been demonstrated to work constantly and safely in higher vertebrates, including fish, avian, mammal and human. For example, almost all of the siRNA agents are based on a double-stranded RNA (dsRNA) conformation, which has been shown to cause interferon-mediated non-specific RNA degradation in vertebrates (Stark et al. (1998) *Annu. Rev. Biochem.* 67: 227-264; Elbashir et al. supra; U.S. Pat. No. 4,289,850 to Robinson; U.S. Pat. No. 6,159,714 to Lau). Such an interferon-mediated cytotoxic response reduces the target specificity of siRNA-induced gene silencing effects and often results in global RNA degradation in vertebrate cells (Stark et.al. supra; Elbashir et al. supra). Especially in mammalian cells, it has been noted that the RNAi effects are disturbed when the siRNA/dsRNA size is longer than 25 base-pairs (bp) (Elbashir et al. supra). Transfection of siRNA or small hairpin RNA (shRNA) sized less than 25 bp may not completely overcome such a problem, because both Sledz et al. ((2003) *Nat Cell Biol.* 5: 834-839) and Lin et al. ((2004b) *Intrn'l J Oncol.* 24: 81-88) have reported that the high dosage of siRNAs and shRNAs (such as >250 nM in human T cells) is able to cause strong cytotoxic effects similar to those of long dsRNAs. This toxicity is due to their double-stranded RNA conformation, which activates the interferon-mediated non-specific RNA degradation and programmed cell death through the signaling pathways of cellular PKR and 2-5A systems. It is well known that interferon-induced protein kinase PKR can trigger cell apoptosis, while activation of interferon-induced 2',5'-oligoadenylate synthetase (2-5A) system leads to extensive cleavage of single-stranded RNAs (i.e. mRNAs) (Stark et al. supra). Both PKR and 2-5A systems contain dsRNA-binding motifs, which possess high affinity to the double-stranded RNA conformation. Further, the most difficult problem is that it is impossible to deliver these small and unstable siRNA/shRNA constructs in vivo due to the abundant RNase activities in higher vertebrates (Brantl S. (2002) *Biochimica et Biophysica Acta* 1575, 15-25).

As the RNAi effects are naturally caused by the production of small RNA products (21-25 nucleotide bases) from a transcriptional template derived from foreign transgenes or viral genomes (Grant, S. R. (1999) supra; Lin et al. (2001) supra), recent utilization of Pol-III-mediated siRNA/shRNA expression vectors has offered relatively stable RNAi efficacy in vivo (Tuschl et al. (2002) *Nat Biotechnol.* 20: 446-448). Although prior arts (Miyagishi et al. (2002) *Nat Biotechnol* 20: 497-500; Lee et al. (2002) *Nat Biotechnol* 20: 500-505; Paul et al. (2002) *Nat Biotechnol* 20: 505-508) attempting to use such a vector-based siRNA approach have succeeded in maintaining constant gene silencing effects, their strategies failed to focus the RNAi effects on a targeted cell or tissue population because of the use of ubiquitous type III RNA polymerase (Pol-III) promoters. Pol-III promoters, such as U6 and H1, are activated in almost all cell types, making tissue-specific gene targeting impossible. Moreover, because the leaky read-through activity of Pol-III transcription often occurs on a short DNA template in the absence of proper termination, large RNA products longer than desired 25 bp can be synthesized and cause unexpected interferon cytotoxicity (Gunnery et al. (1999) *J Mol Biol.* 286: 745 757; Schramm et al. (2002) *Genes Dev* 16: 2593-2620). Such a problem can also result from the competitive conflict between the Pol-III promoter and another vector promoter (i.e. LTR and CMV promoters). Furthermore, it is recently noted that high siRNA/shRNA concentrations generated by the Pol-III-directed RNAi systems can over-saturate the cellular native microRNA (miRNA) pathway and thus cause global miRNA inhibition and cell death (Grimm et al. (2006) *Nature* 441: 537-541). These disadvantages discourage the use of Pol-III-based RNAi vector systems in health care.

In sum, in order to improve the delivery stability, targeting specificity and safety aspects of modern RNAi technologies for skin health care, a better induction and maintenance strategy is highly desired. Therefore, there remains a need for an effective, stable and safe gene modulation method as well as agent composition for suppressing unwanted gene function in skins, using the novel RNAi mechanisms.

SUMMARY OF THE INVENTION

Research based on gene transcript (e.g. mRNA), an assembly of protein-coding exons, is fully described throughout the literature, taking the fate of spliced non-coding introns to be completely digested for granted (Nott et al. (2003) *RNA* 9: 607-617). Is it true that the intron portion of a gene is destined to be a genetic waste without function, or there is a function for it which has not yet been discovered? Recently, this misconception was corrected by the observation of intronic microRNA (miRNA) (Lin et al. (2003) *Biochem Biophys Res Commun.* 310: 754-760; Ying et al (2004) *Gene* 342: 25-28; Ying et.al. (2005) *Biochem Biophys Res Commun.* 326: 515-520). Intronic miRNA is a new class of small single-stranded regulatory RNAs derived from the gene introns, which are spliced out of the precursor messenger RNA (pre-mRNA) of the encoding gene and further processed into small hairpin-like miRNAs. MiRNA is usually about 18-27 nucleotides (nt) in length and is capable of either directly degrading its messenger RNA (mRNA) target or suppressing the protein translation of its targeted mRNA, depending on the complementarity between the miRNA and its target. In this way, the intronic miRNA is functionally similar to previously described siRNA/shRNA, but differs from them in the requirement for the intracellular processes of type II RNA polymerase (Pol-II) transcription and RNA splicing for its biogenesis (Lin et al. (2003) supra). Also, because introns naturally contain multiple translational stop codons for recognition by the intracellular nonsense-mediated decay (NMD) system (Zhang et al. (1994) *Nature* 372: 809-812; Lewis et al. (2003) *Proc. Natl. Acad. Sci. USA* 100: 189-192), most of the unstructured intron sequences can be quickly degraded after RNA splicing to prevent excessive accumulation, which is toxic to the cells. It has been measured that approximately 10%-30% of a spliced intron is preserved after the NMD digestion and further exported to cytoplasm with a moderate half-life, indicating the cellular origin of native intronic miRNAs (Clement et al. (1999) *RNA* 5: 206-220).

As shown in FIG. 1, the natural intronic miRNA biogenesis relies on the coupled interaction between nascent Pol-III-mediated pre-mRNA transcription and intron splicing/excision, occurring within certain nuclear regions proximal to genomic perichromatin fibrils (Lin et al. (2004a) supra; Ghosh et al. (2000) RNA 6: 1325-1334). In eukaryotes, protein-coding gene transcripts, such as mRNAs, are produced by type-II RNA polymerases (Pol-II). The transcription of a genomic gene generates precursor messenger RNA (pre-mRNA), which contains four major parts including 5'-untranslated region (UTR), protein-coding exon, non-coding intron and 3'-UTR. Broadly speaking, both 5'- and 3'-UTR can be seen as a kind of intron extension. Introns occupy the largest proportion of non-coding sequences in the pre-mRNA. Each intron may range up to thirty or so kilo-bases and is required to be excised out of the pre-mRNA content before mRNA maturation. This process of pre-mRNA excision and intron removal is called RNA splicing, which is executed by intracellular spliceosomes. After RNA splicing, some of the intron-derived RNA fragments are further processed to form microRNA (miRNA) derivative molecules, which can effectively silence their targeted genes, respectively, through an RNA interference (RNAi)-like mechanism, while exons of the pre-mRNA are ligated together to form a mature mRNA for protein synthesis.

We have demonstrated that effective mature miRNAs can be generated from the introns of vertebrate genes, of which the biogenetic process is different from those of siRNA and intergenic miRNA (Lin et al. (2003) supra; Lin et.al. (2005) *Gene* 356: 32-38). To demonstrate such differences, FIG. 2 shows the comparison of native biogenesis and RNAi mechanisms among siRNA, intergenic (exonic) miRNA and intronic miRNA. Presumably, siRNA is formed by two perfectly complementary RNAs transcribed by two reversely positioned promoters from one DNA template, then hybridized and further processing into 20-25 bp duplexes by RNaseIII endoribonucleases, namely Dicer. Different from this siRNA model, the biogenesis of intergenic miRNAs, e.g. lin-4 and let-7, involves a long non-coding precursor RNA transcript, or a primary transcript (pri-miRNA), which is directly transcribed from either Pol-II or Pol-III RNA promoters, whereas intronic pri-miRNA is co-transcribed with its encoding gene by only Pol-II and released after RNA splicing as a spliced intron. In the cell nucleus, the pri-miRNA is further excised by either Drosha-like RNases (for intergenic miRNA) or NMD machineries (for intronic miRNA) to form a hairpin-like stem-loop precursor, termed pre-miRNA, and then exported to cytoplasm for processing into mature miRNA by miRNA-associated Dicer (Dicer*). Subsequently, all three small regulatory RNAs are finally incorporated into a RNA-induced silencing complex (RISC), which contains either strand of siRNA or the single strand of miRNA. The Dicers and RISCs for siRNA and miRNA pathways are known to be different (Tang, G. (2005) *Trends Biochem Sci.* 30: 106-114). As a result, the effect of miRNA is generally more specific and less adverse than that of siRNA because only one strand is involved. On the other hand, siRNAs primarily trigger mRNA degradation, whereas miRNAs can induce either mRNA degradation or suppression of protein synthesis, or both, depending on the sequence complementarity to their targeted gene transcripts. Because the intronic miRNA pathway is well coordinated by multiple intracellular regulation systems, including Pol-II transcription, RNA splicing and NMD processing, the gene silencing effect of intronic miRNA is considered to be most effective, specific and safe in all three RNAi pathways (Lin et al. (2008) *Frontiers in Bioscience* 13: 2216-2230).

Our present invention discloses a novel function of intron in the aspect of gene regulation and its relative utilities thereof. As shown in FIG. 3A and FIG. 3B, based on the intronic RNA splicing and processing mechanisms, one preferred embodiment of the present invention is a Pol-II-mediated recombinant gene expression system containing at least a splicing-competent intron, namely SpRNAi, which is able to inhibit the function of a unwanted gene with high complementarity to the intron sequence. The SpRNAi is co-transcribed with the precursor mRNA (pre-mRNA) of the recombinant gene by Pol-II RNA polymerases (P) and cleaved out of the pre-mRNA by RNA splicing. Subsequently, the spliced SpRNAi was further processed into mature gene silencing agents, such as shRNA and miRNA, capable of triggering RNAi-related gene silencing. After intron removal, the exons of the recombinant gene transcript are linked together to form a mature mRNA molecule for translational synthesis of a marker or functional protein.

As shown in FIG. 3A, the essential components of the SpRNAi intron include several consensus nucleotide elements, consisting of a 5'-splice site, a branch-point motif (BrP), a poly-pyrimidine tract (PPT), and a 3'-splice site. In addition, a hairpin shRNA-like pre-miRNA sequence is inserted inside the SpRNAi intron located between the 5'-splice site and the branch-point motif (BrP). This portion of the intron would normally form a lariat structure during RNA splicing and processing. We have observed that spliceosomal U2 and U6 snRNPs, both helicases, are involved in the unwinding and excision of the lariat RNA fragment into pre-miRNA; however, the detailed processing remains to be elucidated. Further, the 3'-end of the SpRNAi construct contains a multiple translational stop codon region (T codon) in order to increase the accuracy of intronic RNA splicing and NMD processing. When presented in a cytoplasmic mRNA, this T codon would signal the activation of the nonsense-mediated decay (NMD) pathway to degrade any unstructured RNA accumulation in the cell. However, the highly secondary structured shRNA and pre-miRNA insert will be preserved for further Dicer cleavage, so as to form mature siRNA and miRNA, respectively. Moreover, for intracellular expression, we manually incorporate the SpRNAi construct in the DraII restriction site of a red fluorescent protein (RGFP) gene isolated from mutated chromoproteins of the coral reef *Heteractis crispa*, so as to form a recombinant SpRNAi-RGFP gene. The cleavage of RGFP at its 208th nucleotide site by the restriction enzyme DraII generates an AG-GN nucleotide break with three recessing nucleotides in each end, which will form 5'- and 3'-splice sites respectively after the SpRNAi insertion. Because this intronic insertion disrupts the structure of a functional RGFP protein, which can be recovered by intron splicing, we can determine the release of intronic shRNA/miRNA and RGFP-mRNA maturation through the appearance of red RGFP around the affected cells. The RGFP gene also provides multiple exonic splicing enhancers (ESEs) to increase RNA splicing accuracy and efficiency.

In another preferred embodiment (FIG. 3B), the present invention provides a genetic engineering method for using synthetic RNA splicing and processing elements, such as 5'-splice site, branch-point motif (BrP), poly-pyrimidine tract (PPT), and 3'-splice site, to form an artificial SpRNAi intron containing at least a desired RNA insert for antisense RNA, small hairpin RNA (shRNA) and/or microRNA (miRNA) production. A DNA synthesizer can chemically produce and linked these elements. Alternatively, the linkage of these elements can be achieved by enzymatic restriction and ligation. The intron so obtained can be used directly for transfection into cells of interest or further incorporated into a cellular gene for co-expression along with the gene transcript (i.e. pre-mRNA) by Pol-II. During RNA splicing and mRNA maturation, the desired RNA insert will be excised and released by intracellular spliceosome and NMD mechanisms and then triggers a desired gene silencing effect on specific gene transcripts with high complementarity to the inserted RNA sequence, while the exons of the recombinant gene transcript are linked together to form mature mRNA for expression of a desirable gene function, such as translation of a reporter or marker protein selected from the group of red/green fluorescent protein (RGFP/EGFP), luciferase, lac-Z, and their derivative homologues. The presence of the reporter/marker protein is useful for locating the production of the inserted shRNA/miRNA molecules in affected cells, facilitating the identification of the desired gene silencing/RNAi effects.

In accordance with the present invention, mature mRNA formed by the linkage of exons may also be useful in conventional gene therapy to replace impaired or missing gene function, or to increase specific gene expression. In another aspect, the present invention provide novel compositions and means for inducing cellular production of gene silencing molecules through intronic RNA splicing and processing mechanisms to elicit either antisense-mediated gene knockout or RNA interference (RNAi) effects, which are useful for inhibiting targeted gene function. The intron-derived gene silencing molecules so obtained include antisense RNA, ribozyme, short temporary RNA (stRNA), double-stranded RNA (dsRNA), small interfering RNA (siRNA), tiny non-coding RNA (tncRNA), short hairpin RNA (shRNA), microRNA (miRNA), and RNAi-associated precursor RNA constructs (pri-/pre-miRNA). The use of these intronic RNA-derived gene silencing agents is a powerful tool for targeting and silencing unwanted genes selected from the group consisting of pathogenic transgenes, viral genes, mutant genes, oncogenes, disease-related small RNA genes and any other types of protein-coding as well as non-coding genes.

Using this Pol-II-mediated SpRNAi-RGFP expression system of the present invention, we have successfully generated mature shRNA and miRNA molecules with full gene silencing capacity in human prostate cancer LNCaP, human cervical cancer HeLa and rat neuronal stem HCN-A94-2 cells (Lin et al. (2006a) *Methods Mol Biol.* 342: 295-312) as well as in zebrafish, chicken and mouse in vivo (Lin et al. (2006b) *Methods Mol Biol.* 342: 321-334). We have tested different pre-miRNA insert constructs targeting against green EGFP and other cellular gene expression in zebrafish and various human cell lines, and have learned that effective gene silencing miRNAs are derived from the 5'-proximity of the intron sequence between the 5'-splice site and the branching point. As shown in FIG. 3C, a strong gene silencing effect occurs only in the transfection of anti-EGFP pre-miRNA insert (lane 4), whereas no effect can be detected in those of other inserts indicated by lanes from left to right: 1, blank vector control (Ctl); 2, pre-miRNA insert targeting HIV-p24 (mock); 3, antisense EGFP insert without the hairpin loop structure (anti); and 5, reverse pre-miRNA sequence which is completely complementary to the anti-EGFP pre-miRNA (miR*). No effect was detected on off-target genes, such as marker RGFP and house-keeping β-actin, suggesting that such intronic miRNA-mediated RNA interference (RNAi) is highly target-specific. To further confirm the role of RNA splicing in this intronic RNAi effect, we have also tested three different SpRNAi-RGFP expression systems as shown in FIG. 3D by lanes from left to right: 1, vector expressing intron-free RGFP without any pre-miRNA insert; 2, vector expressing RGFP with an intronic anti-EGFP pre-miRNA insert; and 3, vector similar to the 2 construct but with a defective 5'-splice site in the SpRNAi intron. As a result of this, Northern bolt analysis shows that mature miRNA is released only from the spliced intron of the vector 2 construct, which is exactly identical to the SpRNAi vector construct with the anti-EGFP pre-miRNA insert in the FIG. 3C, indicating the requirement of cellular RNA splicing for intronic miRNA biogenesis.

After the above understanding, we have further determined the optimal structural design of the pre-miRNA inserts for inducing maximal gene silencing effects and learned that a strong structural bias exists in the cellular selection of a mature miRNA strand during assembly of the RNAi effector, the RNA-induced gene silencing complex (RISC) (Lin et.al. (2005) *Gene* 356: 32-38). RISC is a protein-RNA complex that directs either target gene transcript degradation or translational repression through the RNAi mechanism. Formation of siRNA duplexes plays a key role in assembly of the siRNA-associated RISC. The two strands of the siRNA duplex are functionally asymmetric, but assembly into the RISC complex is preferential for only one strand. Such preference is determined by the thermodynamic stability of each 5'-end base-pairing in the strand. Based on this siRNA model, the formation of miRNA and its complementary miRNA (miRNA*) duplexes was thought to be an essential step in the assembly of miRNA-associated RISC. If this were true, no functional bias would be observed in the stem-loop structure of a pre-miRNA. Nevertheless, we observed that the stem-loop orientation of the intronic pre-miRNA is involved in the strand selection of a mature miRNA for RISC assembly in zebrafish.

As shown in FIG. 4A, we have constructed two different intronic miRNA-inserted SpRNAi-RGFP expression vectors containing a pair of symmetric pre-miRNA constructs, namely miRNA*-stemloop-miRNA [1] and miRNA-stemloop-miRNA* [2], respectively. Both pre-miRNAs contain the same double-stranded stem-arm structure, which is directed against the EGFP nucleotide 280-302 sequence. In definition here, miRNA refers the exactly complete sequence of a mature microRNA, while miRNA* refers the reverse nucleotide sequence complementary to the mature microRNA sequence. After liposomal transfection of these miRNA-expressing SpRNAi-RGFP vectors (60 μg each) into two-week-old zebrafish larvae for 24 hours (Lin et.al. (2005) supra), we have isolated the zebrafish small RNAs using mirVana miRNA isolation columns (Ambion, Austin, Tex.) and then precipitated all the potential miRNAs matched to the targeted EGFP region by latex beads containing the target sequence. After sequencing, one effective miRNA identity, miR-EGFP(280-302), is identified to be active in the transfections of the 5'-miRNA-stemloop-miRNA*-3' construct [2], as shown in FIG. 4A (gray-shading sequences). Since the mature miRNA is detected only in the zebrafish transfected by the [2] 5'-miRNA-stemloop-miRNA*-3' construct, the miRNA-associated RISC must preferably interact with the construct [2] rather than the [1] pre-miRNA, demonstrating the existence of a structural bias for intronic miRNA-RISC assembly. In this experiment, we use an actin-promoter-deriven Tg(UAS:gfp) strain zebrafish, namely Tg(actin-GAL4:UAS-gfp), which constitutively express a green fluorescent EGFP protein in almost all cell types of the fish body. As shown in FIG. 4B, transfection of the SpRNAi-RGFP vector in these zebrafish silences the targeted EGFP and co-expresses a red fluorescent marker protein RGFP, serving as a positive indicator for intronic miRNA generation in the affected cells. The gene silencing effect in the gastrointestinal (GI) tract is somehow lower than other tissues, probably due to the high RNase activity in this region. Based on further Western blot analysis (FIG. 4C), the indicator RGFP protein expression is detected in both of the fish transfected with either 5'-miRNA*-stemloop-miRNA-3' or 5'-miRNA-stemloop-miRNA*-3' pre-miRNA, whereas gene silencing of the target EGFP expression (green) only occurs in the fish transfected with the 5'-miRNA-stemloop-miRNA*-3' pre-miRNA construct [2], confirming the result of FIG. 4B. Because thermostability of the 5'-end stem-arm of both pre-miRNA constructs is the same, we conclude that the stem-loop of the intronic pre-miRNA is involved in the strand selection of a mature miRNA sequence during RISC assembly. Given that the cleavage site of Dicer in the stem-arm is known to determine the strand selection of mature miRNA (Lee et al. (2003) *Nature* 425: 415-419), the stem-loop of an intronic pre-miRNA may function as a determinant for the recognition of the special cleavage site.

In the above early design, because the over sizes of many native pre-miRNA stem-loop structures cannot fit in the SpRNAi-RGFP expression vector for efficient expression, we must use a short tRNA$^{met}$ loop (i.e. 5'-(A/U)UC-CAAGGGGG-3') (SEQ ID NO: 26) to replace the native pre-miRNA loops. The tRNA$^{met}$ loop has been shown to efficiently facilitate the export of designed miRNAs from nucleus to cytoplasm through the same Ran-GTP and Exportin-5 transporting mechanisms (Lin et al. (2005) supra). Currently, the present invention uses a pair of manually improved pre-mir-302 loops (i.e. 5'-GCTAAGCCAGGC-3' (SEQ.ID.NO.1) and 5'-GCCTGGCTTAGC-3' (SEQ. ID.NO.2)), which provide the same nuclear export efficiency as the native pre-miRNAs but not interfere with the tRNA exportation. The design of these new pre-miRNA loops is based on a mimicking modification of short stem-loops of mir-302s, which are highly expressed in embryonic stem cells but not in other differentiated tissue cells. Thus, the use of these man-made pre-miRNA loops will not interfere with the native miRNA pathway in our body.

For pre-miRNA insertion, because the intronic insertion site of the recombinant SpRNAi-RGFP gene is flanked with a PvuI and an MluI restriction site at its and 5'-ends 3'-ends, respectively, the primary intronic insert can be easily removed and replaced by various gene-specific pre-miRNA inserts (e.g. anti-EGFP and anti-Tyr pre-miRNA) possessing matched cohesive ends. By changing the pre-miRNA inserts directed against different gene transcripts, this intronic miRNA generation system can be served as a powerful tool for inducing targeted gene silencing in vitro and in vivo. For confirming the correct insert size, the pre-miRNA-inserted SpRNAi-RGFP gene (10 ng) can be amplified by a polymerase chain reaction (PCR) with a pair of oligonucleotide primers (i.e. 5'-CTCGAGCATG GTGAGCGGCC TGCT-GAA-3' (SEQ ID NO: 21) and 5'-TCTAGAAGTT GGCCT-TCTCG GGCAGGT-3' (SEQ ID NO: 22)) for 25 cycles at 94° C., 52° C. and then 70° C. each for 1 min. The resulting PCR products are fractionated on a 2% agarose gel, and then extracted and purified by gel extraction kit (Qiagen, Calif.) for sequencing confirmation.

The present invention adopts the proof-of-principle design of the Pol-II-mediated SpRNAi-RGFP expression system and uses it for developing new cosmetic products for skin care. In one preferred embodiment, the present invention provides a method for using a non-naturally occurring intron and its components capable of being processed into small hairpin RNA (shRNA) and/or microRNA (miRNA) molecules by skin cells and thus inducing specific gene silencing effects on skin pigment-related genes and/or aging-causing genes in the cells, comprising the steps of: a) providing: i) a skin substrate expressing a targeted gene, and ii) an expression-competent composition comprising a recombinant gene capable of producing an intron-encoding primary RNA transcript, which is in turn able to generate a pre-designed gene silencing molecule from the encoded intron through intracellular RNA splicing and processing mechanisms and thus to knock down the targeted gene expression or to suppress the targeted gene function in the skin substrate; b) treating the skin substrate with the composition under conditions such that the targeted gene function in the skin substrate is inhibited. The skin substrate can express the targeted gene either in vitro, ex vivo or in vivo. In one aspect, the RNA splicing- and processing-generated gene silencing molecule is a hairpin-like pre-miRNA insert located within the intron area of the recombinant gene and is capable of silencing a targeted gene selected from the group consisting of tyrosinase (Tyr), hyaluronidase (Hyal), hyaluronan receptors CD44 and CD168, NF-kappa B, and other pigmentation-related and/or aging-related genes and oncogenes. Alternatively, such a pre-miRNA insert can also be artificially incorporated into the intron region of a cellular gene in the skin. In general, this kind of intronic insertion technology includes plasmid-like transgene transfection, homologous recombination, transposon delivery, jumping gene integration and retroviral infection.

In another aspect, the recombinant gene of the present invention expresses a construct reminiscent of a pre-mRNA structure. The recombinant gene is consisted of two major different parts: exon and intron. The exon part is ligated after RNA splicing to form a functional mRNA and protein for identification of the intronic RNA release, while the intron part is spliced out of the recombinant gene transcript and further processed into a desired intronic RNA molecule, serving as a gene silencing effector, including antisense RNA, miRNA, shRNA, siRNA, dsRNA and their precursors (i.e. pre-miRNA and piRNA). These desired intronic RNA molecules may comprise a hairpin-like stem-loop structure containing a sequence motif homologous to 5'-GCTAAGC-CAG GC-3' (SEQ.ID.NO.1) or 5'-GCCTGGCTTA GC-3' (SEQ.ID.NO.2), which facilitates not only accurate excision of the desired RNA molecule out of the intron but also nuclear exportation of the desired RNA molecule to the cell cytoplasm. Also, the stem-arms of these intron-derived RNA molecules contain homology or complementarity, or both, to a targeted gene or a coding sequence of the targeted gene transcript. The homologous or complementary sequences of the desired RNA molecules are sized from about 15 to about 1,500 nucleotide bases, most preferably in between about 18 to about 27 nucleotide bases. The homology and/or complementarity rate of the desired intronic RNA molecule to the targeted gene sequence is ranged from about 30~100%, more preferably 35~49%, for a desired hairpin-like intronic RNA and 90~100% for a linear intronic RNA molecule.

In addition, the 5'-end of the non-naturally occurring intron contains a donor splice site homologous to either 5'-GTAAGAGK-3' (SEQ.ID.NO.3) or GU(A/G)AGU motifs (i.e. 5'-GTAAGAGGAT-3' (SEQ ID NO: 27), 5'-GTAAGAGT-3', 5'-GTAGAGT-3' and 5'-GTAAGT-3'), while its 3'-end is a acceptor splice site that is homologous to either GWKSCYRCAG (SEQ.ID.NO.4) or CT(A/G)A(C/T)NG motifs (i.e. 5'-GATATCCTGC AG-3' (SEQ ID NO: 28), 5'-GGCTGCAG-3' and 5'-CCACAG-3'). Moreover, a branch point sequence is located between the 5'- and 3'-splice sites, containing homology to 5'-TACTWAY-3' (SEQ.ID.NO.5) motifs, such as 5'-TACTAAC-3' and 5'-TACTTAT-3'. The adenosine "A"nucleotide of the branch-point sequence forms a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ.ID.NO.6) or 5'-(TC)nNCTAG(G/-)-3' (SEQ.ID.NO.7) motifs. The symbols of "m"and "n"indicate multiple repeats ≥1; most preferably, the m number is equal to 1~3 and the n number is equal to 7~12. The symbol "-"refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U).

In another preferred embodiment of the present invention, the recombinant gene composition can be cloned into an expression-competent vector for gene transfection. The expression-competent vector is selected from a group consisting of plasmids, cosmids, phagemids, yeast artificial chromosomes, jumping genes, transposons, retrotransposons, retroviral vectors, lentiviral vectors, lambda vectors, adenoviral (AMV) vectors, adeno-associated viral (AAV) vectors, modified hepatitis-viral (HBV) vectors, cytomegalovirus (CMV)-associated viral vectors, and plant-associated mosaic virus, such as tabacco mosaic virus (TMV), tomato mosaic virus (ToMV), Cauliflower mosaic virus (CaMV) and poplar mosaic virus (PopMV). During transfection of the SpRNAi-RGFP gene, multiple vectors expressing different intronic gene silencing effectors may be used to achieve gene silencing effects on a single gene or multiple target genes. Alternatively, multiple gene silencing effectors may be generated from the intronic hairpin RNA insert of the SpRNAi-RGFP gene to provide multiple gene silencing effects. The strength of this strategy is in its delivery stability through the use of vector-based transgene transfection and viral infection, providing a stable and relatively long-term effect of specific gene silencing. In one aspect, the present invention via cellular RNA splicing and processing mechanisms can produce RNAi-related gene silencing molecules, including small interfering RNA (siRNA), microRNA (miRNA) and/or small hairpin RNA (shRNA), intracellularly under the control of a gene-specific RNA promoter, such as type-II RNA polymerase (Pol-II) promoters and viral promoters, or both. The viral promoters may include RNA promoters and their derivatives isolated from cytomegalovirus (CMV), retrovirus long-terminal region (LTR), hepatitis B virus (HBV), adenovirus (AMV), adeno-associated virus (AAV), and plant-associated mosaic virus. For example, a lentiviral LTR promoter is sufficient to provide up to $5 \times 10^5$ copies of pre-mature mRNA per cell. It is feasible to insert a drug-sensitive repressor in front of the lentiviral promoter in order to control the expression rate. The repressor can be inhibited by a chemical drug or antibiotics selected from the group of G418, tetracycline, neomycin, ampicillin, kanamycin, and their derivatives, etc.

In addition to the presently invented skin care utilizations, the potential applications of the present invention may include skin therapy by suppression of disease-related genes, epidermal vaccination directed against viral genes, external treatment of microbe-related pathogens, research of signal transduction pathways in skins, and high throughput screening of gene functions in conjunction with microarray technologies, etc. The present invention can also be used as a tool for studying gene function in skins or providing a composition and method for altering the characteristics of a skin type. The skin type can be selected from the group of normal, pathogenic, cancerous, virus-infected, microbe-infected, physiologically diseased, and genetically mutated animal or human skins.

The present invention provides a novel means of producing intronic RNA molecules in cell as well as in vivo through RNA splicing and processing mechanisms, preferably leading to the generation of mature siRNA, miRNA and shRNA molecules capable of inducing RNAi/PTGS-associated gene silencing effects. The desired siRNA, miRNA and/or shRNA molecules can be produced in a single unit or in multiple units, depending on how the cellular mechanisms express and process the intronic precursor miRNA/shRNA inserts of the present invention. For example, it has been reported that the ectopic expression of one anti-EGFP pre-miRNA inserted intron in zebrafish, as shown in FIG. 3A, actually generates two mature microRNAs different sizes, such as miR-EGFP(282/300) and miR-EGFP(280-302), indicating that one gene-silencing RNA insert of the SpRNAi intron can generate more than one gene-silencing RNA effectors. Same or different spliced RNA effectors can be generated in either sense or antisense conformation, or both, complementary to the targeted gene transcript(s). In certain cases, the spliced RNA molecule can hybridize with a targeted gene transcript (i.e. mRNA) to form a double-stranded RNA (dsRNA) for triggering secondary RNAi/PTGS effects. The intronic siRNA, miRNA and/or shRNA are constantly produced by the expression-competent vectors of the present invention, which will alleviate the concerns of fast small RNA degradation for in vivo applications.

Alternatively, the present invention further provides a novel means of producing antisense microRNA (miRNA*) directed against a targeted microRNA (miRNA) gene in skin cells, resulting in the inhibition of the targeted miRNA function. Because the miRNA usually functions in RNAi-associated gene silencing, the miRNA* can neutralize this gene silencing effect and thus may recover the function of the miRNA-suppressed gene(s). Unlike perfectly matched siRNA, the binding of miRNA* to miRNA creates a mismatched base-paired region for RNase cleavage and degradation. Such a mismatched base-paired region is preferably located either in the middle of the stem-arm region or in the stem-loop structure of the miRNA precursor (pre-miRNA). It has been shown that mismatched base-pairing in the middle of siRNA inhibits the gene silencing effect of the siRNA (Holen et al. (2002) Nucleic Acid Res. 30: 1757-1766; Krol et al. (2004) J. Biol. Chem. 279: 42230-42239). Probably similar to intron-mediated enhancement (IME) phenomena in plants, previous studies in Arabidopsis and Nicotiana spp. have indicated that intronic inserts play an important role in posttranscriptional gene modulation for both enhancing and silencing specific gene expression (Rose A. B. (2002) RNA 8: 1444-1451; Stoutjesdijk et al. (2002) Plant Physiol. 129: 1723-1730). The IME mechanism can recover targeted gene expression from 2 fold to over 10 fold by targeting the miRNA(s) complementary to the targeted gene.

BRIEF DESCRIPTION OF THE DRAWINGS.

The patent or application file contains at least one drawing executed in color. Copies of this patent or patent application publication with color drawing(s) will be provided by the office upon request and payment of the necessary fee.

The FIG. 1 depicts the biogenesis of native intronic microRNA (miRNA) that is co-transcribed with precursor messenger RNA (pre-mRNA) by Pol-II and cleaved out of the pre-mRNA by RNA splicing, while the ligated exons become a mature messenger RNA (mRNA) for protein synthesis. The spliced intronic miRNA with an antisense or a hairpin-like secondary structure is further processed into mature miRNA capable of triggering RNAi-related gene silencing effects. Thus, we designed an artificial intron containing at least a precursor microRNA (pre-miRNA) structure, namely SpRNAi, mimicking the biogenesis of the native intronic miRNA (FIGS. 3A and 3B). The SpRNAi is incorporated into a cellular or recombinant gene, which is expressed by type-II RNA polymerases (Pol-I) under the control of either Pol-II or viral RNA promoter (P). Upon intracellular transcription, the gene transcript so produced is subjected to RNA splicing and processing events and therefore releases the pre-designed, intronic RNA molecule in the transfected cell. In certain embodiments, the desired RNA molecule is an antisense RNA construct that can be served as antisense oligonucleotide probes for gene knockdown. In other embodiments, the desired RNA molecule consists of small antisense and sense RNA fragments to function as double-stranded siRNA for RNAi induction. In still other embodiments, the desired RNA molecule is a hairpin-like RNA construct capable of causing RNAi-associated gene silencing effects.

Figure 1:
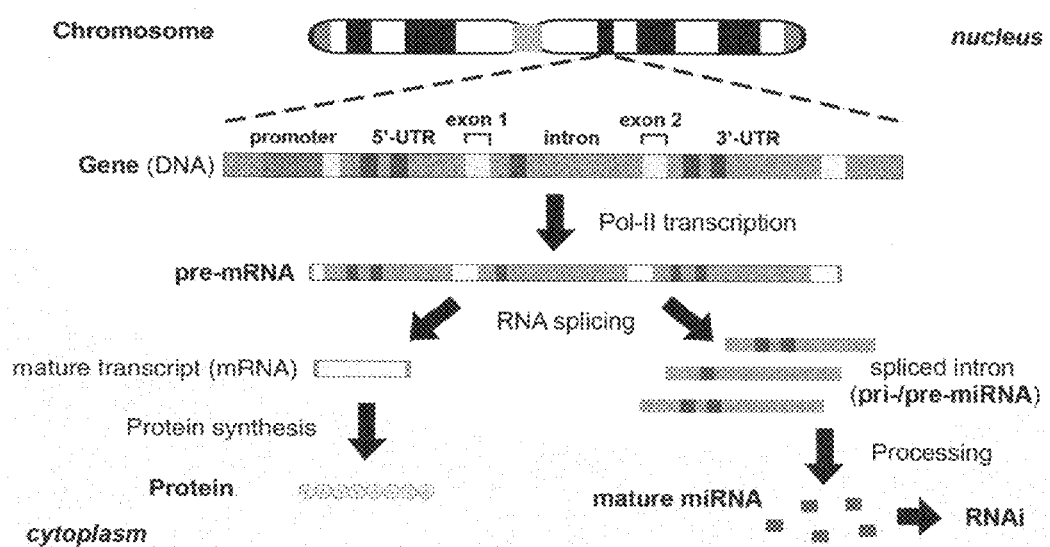

Referring particularly to the drawings for the purpose of illustration only and not limitation, there is illustrated:

FIG. 1 depicts the intracellular mechanism of natural intronic microRNA (miRNA) biogenesis.

Figure 2:
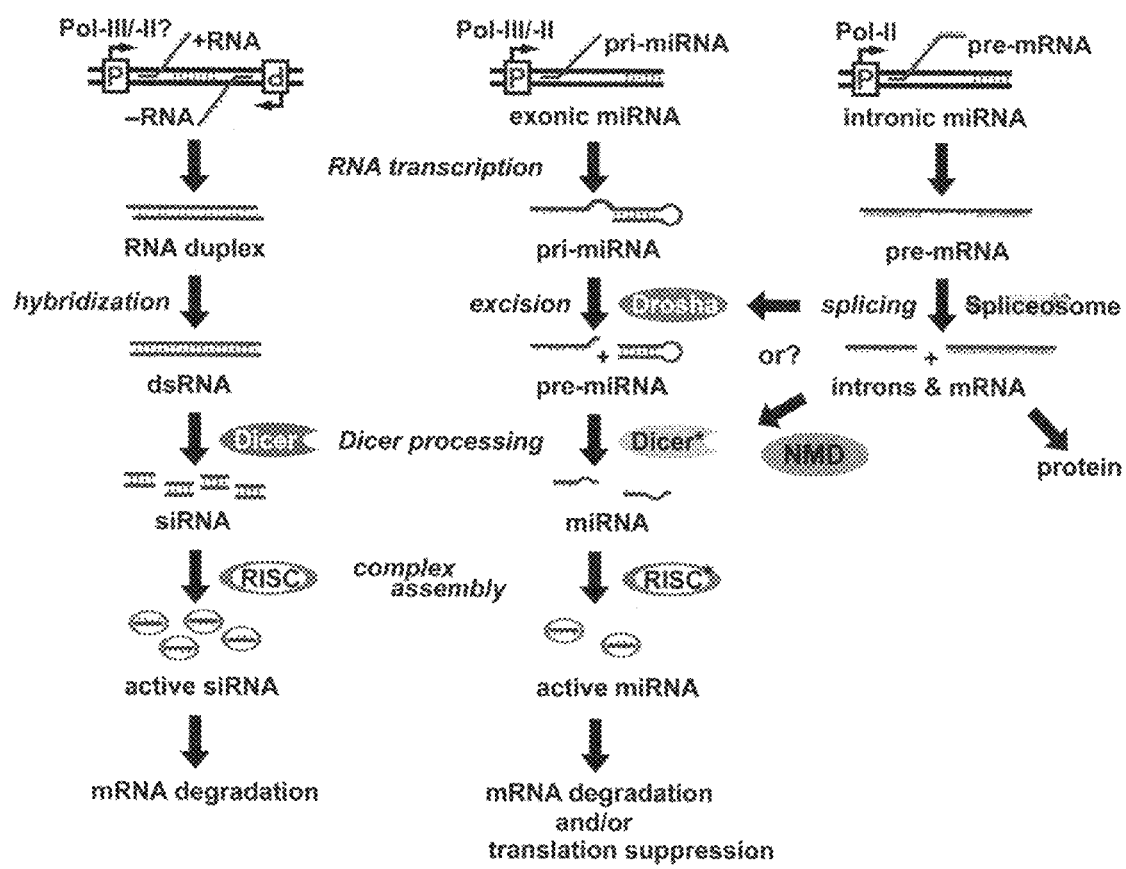

FIG. 2 depicts the different biogenesis mechanisms among the siRNA, exonic (intergenic) microRNA and intronic microRNA pathways.

FIG. 3A-FIG. 3D depicts the preferable embodiment of the SpRNAi-incorporated recombinant gene (SpRNAi-RGFP) construct in an expression-competent vector composition (A)(SEQ ID NO: 29), and the strategy (B) of using this composition to generate man-made microRNA, mimicking the biogenesis of the natural intronic miRNA. In vivo tests of an SpRNAi-RGFP expression composition directed against green EGFP in fish show an over 85% knockdown effect specifically on the targeted EGFP gene expression, as determined by Western blot analysis (C). The intron-derived anti-EGFP microRNA and its spliced precursor can be observed on a 1% formaldehyde agarose gel electrophoresis after Northern blot analysis (D).

Figure 4:
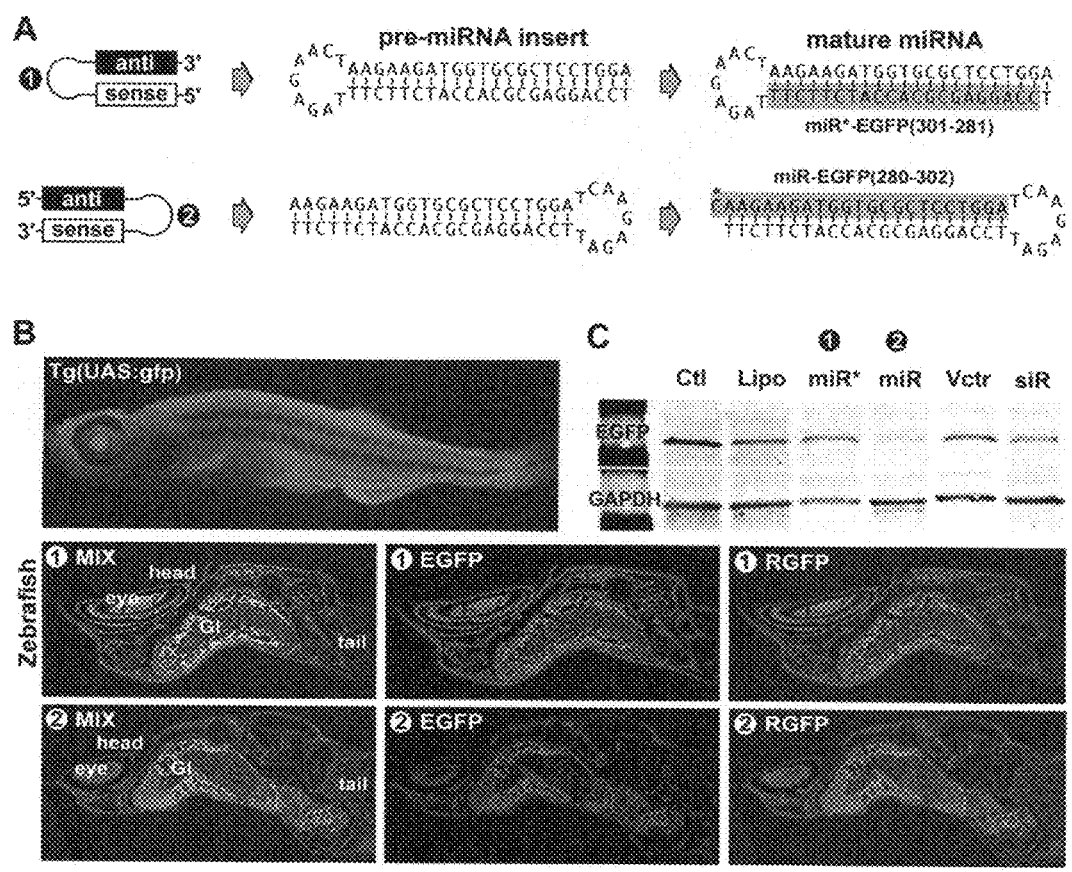

FIG. 4A-FIG. 4C show different designs of intronic RNA inserts in an SpRNAi-RGFP construct for effective microRNA biogenesis and the resulting gene silencing of a targeted green fluorescent protein (EGFP) expression in zebrafish, demonstrating an asymmetric preference in RISC assembly between the transfection of [1] 5'-miRNA*-stem-loop-miRNA-3' (SEQ ID NO: 30) and that of [2] 5'-miRNA-stemloop-miRNA*-3' hairpin RNA structures (SEQ ID NOS: 31 and 32), respectively (A). In vivo gene silencing is only observed in the transfection of the [2] pre-miRNA construct, but not the [1] construct. Since the color combination of EGFP and RGFP displays more red than green (as shown in deep orange), the expression level of target EGFP (green) is significantly reduced in the [2] pre-miRNA transfection, while vector indicator RGFP (red) is evenly present in all vector transfections (B). Western blot analysis of the EGFP protein levels confirms the specific silencing result of the [2] pre-miRNA transfection (C). No detectable gene silencing is observed in fish with other treatments, such as liposome only (Lipo), empty vector without any insert (Vctr), and siRNA (siR).

Figure 5:
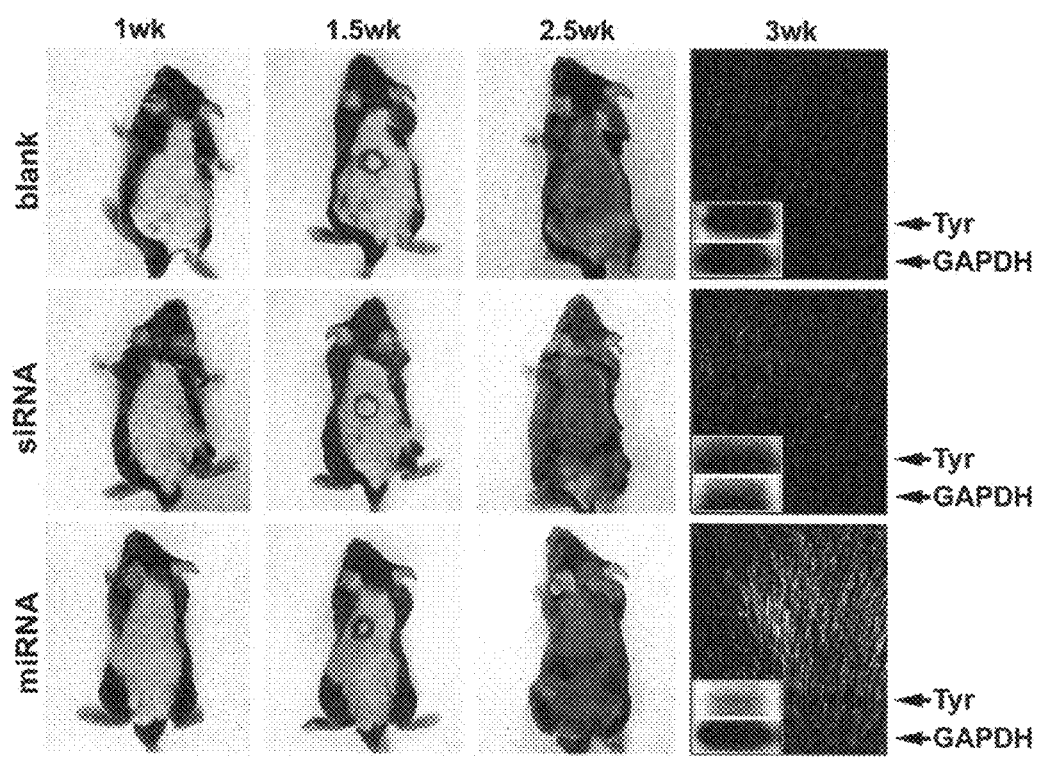

FIG. 5 shows the tyrosinase (Tyr) gene silencing effect of the native mir-434 expressed by the present invention on skin depigmentation in mice, indicating the feasibility of localized skin gene modulation in vivo using the present invention.

Figure 6:
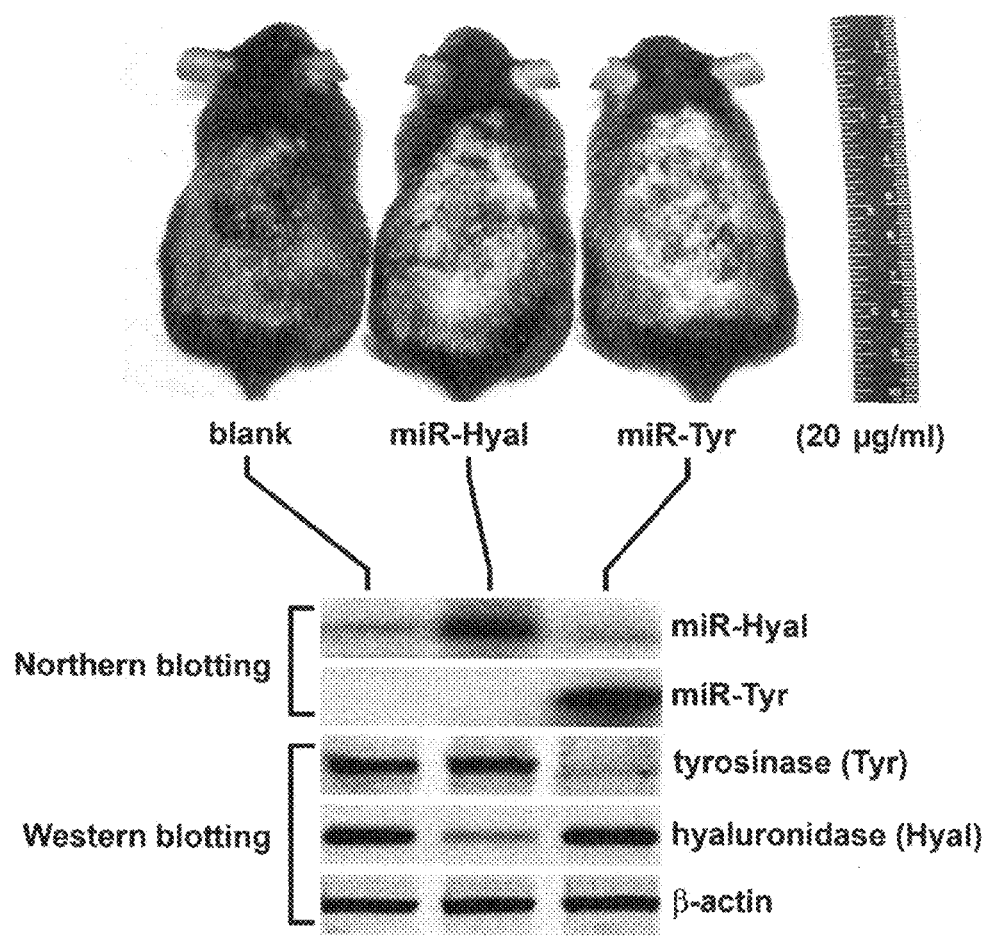

FIG. 6 shows the result of utilization of an improved man-made anti-Tyr pre-miRNA (miR-Tyr) insert expressed by the present invention in the mouse skins, showing a more specific and less off-target gene silencing effect on targeted tyrosinase (Tyr).

Figure 7:
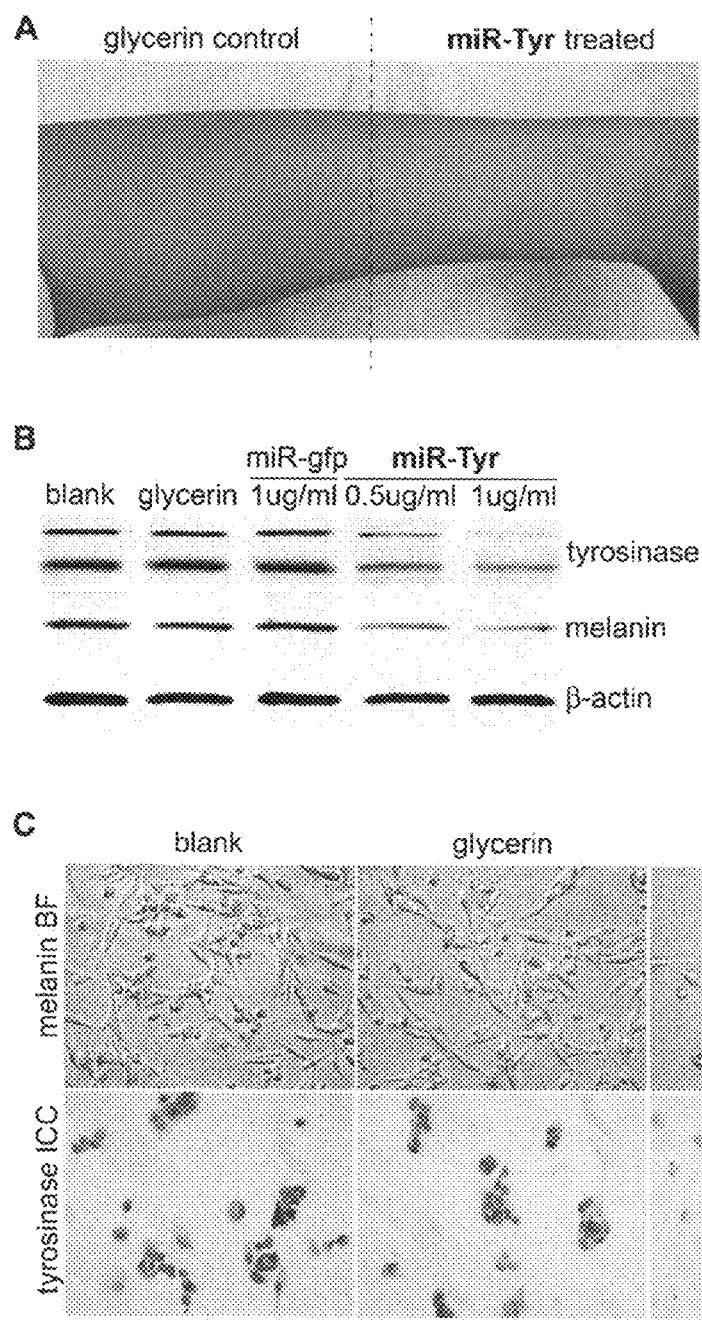

FIG. 7A-FIG. 7C shows the result of utilization of the improved anti-Tyr pre-miRNA (miR-Tyr) insert expressed by the present invention, identical to the FIG. 6 approach, in the human arm skins (A) and primary skin cell cultures (B and C), showing an over 50% knockdown rate in tyrosinase (Tyr) expression.

Figure 8:
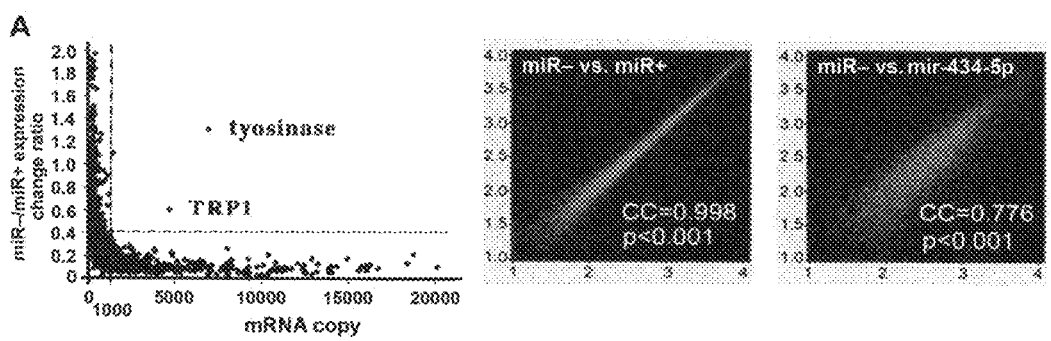
Figure 8:
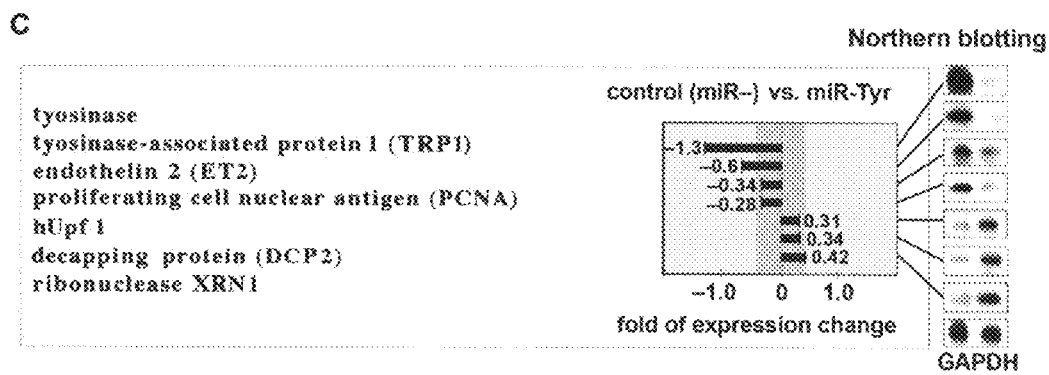

FIG. 8A-FIG. 8C shows the result of gene microarray analysis (Affymetrix human GeneChip U133A&B, CA) of altered gene expression in the above man-made anti-Tyr pre-miRNA-transfected primary skin cell cultures, showing a much more target-specific and less off-target gene silencing effect than the use of native microRNAs, such as mir-434.

DETAILED DESCRIPTION OF THE INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention provides a novel composition and method for altering genetic characteristics of skin cells using intron-derived RNAs. Without being bound by any particular theory, such an alteration of genetic characteristics is directed to a newly discovered intron-mediated gene silencing mechanism, triggered by transfection of a recombinant gene containing at least an RNA splicing-competent intron, namely SpRNAi, in the cell or organism of interest. The SpRVAi intron further carries an intronic RNA insert, which can be released by intracellular RNA splicing and processing machineries and then triggers RNAi/PTGS-related gene silencing effects on targeted gene transcripts that contain high complementarity to the intronic RNA insert. Generally, as shown in FIGS. 4-7, when the recombinant gene is chemically transduced, liposomally transfected, or otherwise introduced by viral infection into the skin cells, the intronic RNA insert is co-transcribed with the recombinant gene by Pol-II and then released from the recombinant gene transcript by RNA splicing and processing machineries, such as spliceosome and nonsense-mediated decay (NMD) systems. After RNA splicing, the intronic RNA forms a lariat RNA and then further processed into small gene silencing effector RNAs, such as short-temporary RNA (stRNA), antisense RNA, small-interfering RNA (siRNA), short-hairpin RNA (shRNA), microRNA (miRNA), Piwi-interacting RNA (piRNA) and/or their precursor RNAs. Consequently, these gene silencing effector RNAs either degrade their targeted gene transcripts or suppress protein translation of the targeted gene transcripts through the functional assembly and action of RNA-induced silencing complex (RISC) and/or RNAi-induced initiator of transcriptional silencing (RITS).

Mimicking the natural pre-mRNA splicing and processing mechanisms, we use intracellular spliceosomal and NMD machineries to catalyze the intron removal and processing of our invented SpRNAi-RGFP expression system. Through a sequential assembly of intracellular spliceosomal components on several snRNP-recognition elements of the SpRNAi intron (e.g. binding sites for snRNPs U1, U2 and U4IU6.U5 tri-snRNP), the SpRNAi intron is released and further processed into small gene silencing effectors. The methods for incorporating the synthetic snRNP-recognition elements into an SpRNAi intron and then incorporating the SpRNAi into the recombinant RGFP gene of the present invention are described in Examples 1-2, respectively. For a spliceosomal intron, the way of sequential assembly of spliceosomal snRNPs to their relative recognition sites is in a generic order in all eukaryotes (Lewin B. (2000) Genes, Seventh Edition, Oxford University press, pp688-690). Due to the wide variety of intracellular RNA-splicing and processing mechanisms in various species, Lewin B. has stated a well known fact that "splice sites are generic . . . And the apparatus for splicing is not tissue specific . . . ", which is said to be a general property for all spliceosomal introns. In nature, the sequential order of intronic RNA splicing processes occurs as follows: first, binding of U1 snRNP to the 5'-intron splicing junction (5'-donor splice site), then binding of U2 snRNP to the branch-point motif, and last, association of the U4/U6.U5 tri-snRNP to the U1 and U2 snRNPs, so as to form an early splicing complex for precisely cleavage of the 5'-splicing junction. After splicing release of the 5'-splicing intron junction, the 3'-splicing intron junction (3'-acceptor splice site) is then cleaved by a late splicing complex formed by U5 snRNP and some other splicing proteins. However, little is known about the protein/protein and RNA/protein interactions that bridge the U4/U6 and U5 snRNP components within a eukaryotic tri-snRNP, and knowledge on the binding sites of proteins on U4/U6 and U5 snRNPs remains largely unclear.

Design, Construction and Assessment of a Pol-II-Mediated Artificially Recombinant SpRNAi-RGFP Gene Expression System Capable of Inducing Intronic RNA-Mediated Gene Silencing Effects in Vivo.

Strategy for triggering desired intracellular RNA splicing- and/or processing-directed gene silencing mechanisms in vivo has been tested, using a Pol-II-transcribed recombinant gene vector of the present invention, namely SpRNAi-RGFP, which contains an artificial splicing-competent intron (SpRNAi) for expressing intronic gene silencing RNA effectors (FIGS. 3A and B), such as microRNA (miRNA) and hairpin-like shRNA. Incorporation of the SpRNAi intron into a red-shifted fluorescent protein gene (RGFP) was genetically engineered by sequential ligation of several synthetic DNA sequences as shown in Examples 1-2. The SpRNAi intron comprises a precursor miRNA or shRNA insert, which can be released by intracellular RNA splicing and processing machineries, such as spliceosomes and NMD system components, then triggers an intronic RNA-mediated gene silencing mechanism through the production of mature miRNA or shRNA gene silencing effectors. Although we show here a model of inducing targeted gene silencing through the intracellular RNA splicing and processing of the recombinant gene transcripts, the same principle can be applied to design and produce intronic gene silencing RNA inserts functioning via the RNA processing of ribosomal precursor RNA (pre-rRNA), which is mainly transcribed by type-I RNA polymerases (Pol-I). Other RNA transcripts capable of being used to express and process the SpRNAi intron include hnRNA, rRNA, tRNA, snoRNA, snRNA, viral RNA, and their precursors as well as derivatives.

Figure 3:
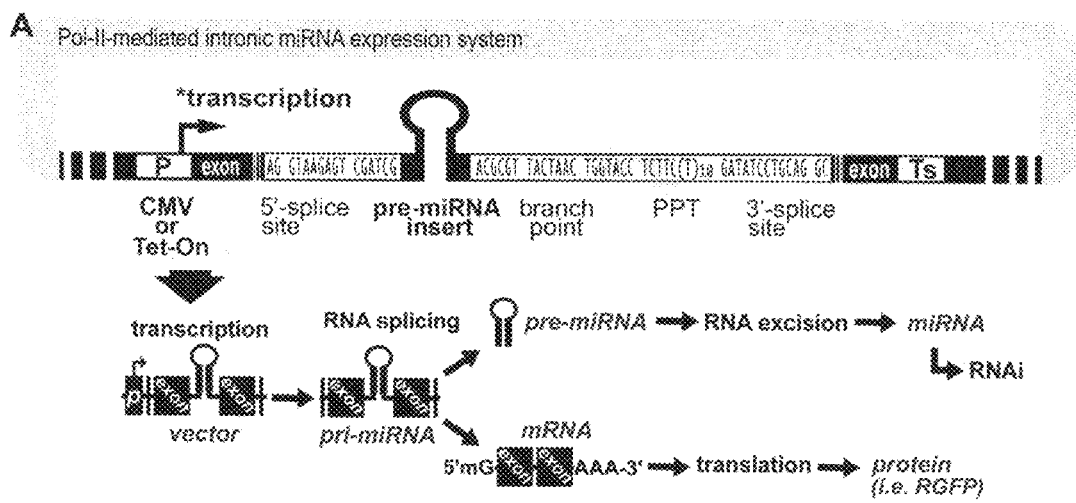
Figure 3:
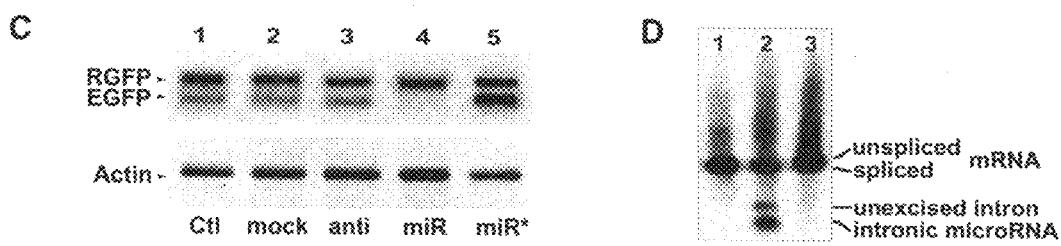

As shown in Examples 1-2 and FIG. 3A, the SpRNAi intron was synthesized and incorporated into an intron-free red-shifted fluorescent protein gene (RGFP or rGFP), which was mutated from the HcRed1 chromoproteins of *Heteractis crispa*. Because the inserted SpRNAi intron(s) disrupted the functional fluorescent protein structure of RGFP, we were able to check the intron removal and mRNA maturation of RGFP gene transcripts through the reappearance of red fluorescent light emission at the 570-nm wavelength in a successfully transfected cell or organism. Construction of this recombinant SpRNAi-RGFP gene was based on the natural structures of a spliceosomal intron in a precursor messenger RNA (pre-mRNA). The major components of a SpRNAi intron include several snRNP recognition sites and linkers, such as 5'-donor (DS) and 3'-acceptor (AS) splice site in the ends for precise cleavage, a branch point motif (BrP) for splicing recognition, a poly-pyrimidine tract (PPT) for spliceosomal interaction, linkers for connection of each of these components and some restriction/cloning sites for desired intronic insertion. Structurally from the 5' to 3' end as shown in FIG. 3B, the SpRNAi intron of the present invention contains a 5'-splice site, an anti-(target gene) intronic insert, a branch point motif (BrP), a poly-pyrimidine tract (PPT), and a 3'-acceptor (AS) splice site for functional spliceosome assembly. In addition, some translational termination codons (T codon) may be located in the linker sequences close to the 3'-splice site of the SpRNAi intron.

Generically, the 5'-donor splice site is a nucleotide sequence containing or homologous to either 5'-GTAAGAGK-3' (SEQ.ID.NO.3) or GU(A/G)AGU motifs (such as 5'-GTAAGAGGAT-3' (SEQ ID NO: 27), 5'-GTAAGAGT-3', 5'-GTAGAGT-3' and 5'-GTAAGT-3'), while the 3'-acceptor splice site is a nucleotide sequence containing or homologous to either GWKSCYRCAG (SEQ.ID.NO.4) or CT(A/G)A(C/T)NG motifs (such as 5'-GATATCCTGC AG-3' (SEQ ID NO: 28), 5'-GGCTGCAG-3' and 5'-CCACAG-3'). Moreover, a branch point sequence is located between the 5'- and 3'-splice sites, containing homology to 5'-TACTWAY-3' (SEQ.ID.NO.5) motifs, such as 5'-TACTAAC-3' and 5'-TACTTAT-3'. The adenosine "A" nucleotide of the branch-point sequence forms a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ.ID.NO.6) or 5'-(TC)nNCTAG(G/-)-3' (SEQ.ID.NO.7) motifs. The symbols of "m" and "n" indicate multiple repeats ≥1; most preferably, the m number is equal to 1~3 and the n number is equal to 7~12. The symbol "-" refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)." For all of the above spliceosomal recognition components, the deoxythymidine (T) nucleotide is replaceable with uridine (U).

To test the function of a spliced SpRrAi insert, various oligonucleotide agents can be cloned into the anti-(target gene) intronic insert site of the recombinant SpRNAi-RGFP gene construct. The anti-(target gene) intronic insert site contains multiple restriction and cloning sites, which are recognized by restriction enzymes selected from the group of AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI endonuclease and the combination thereof. These intronic oligonucleotide inserts are DNA templates encoding highly structural RNAs selected from the group consisting of lariat-form RNA, short-temporary RNA (stRNA), antisense RNA, small-interfering RNA (siRNA), double-stranded RNA (dsRNA), short-hairpin RNA (shRNA), microRNA (miRNA), Piwi-interacting RNA (piRNA), ribozyme, and their precursors as well as derivatives in either sense or antisense conformation, or both, and a combination thereof.

For the convenience of gene delivery and activation in the cell or organism of interest, the recombinant SpRNAi-RGFP gene of the present invention is preferably cloned into an expression-competent vector, selected from the group consisting of plasmid, cosmid, phagmid, yeast artificial chromosome, transposon, jumping gene, viral vector, and the combination thereof. The vector so obtained is introduced into the cell or organism by a high efficient gene delivery method selected from the group consisting of liposomal transfection, chemical transfection, chemical transformation, electroporation, transposon recombination, jumping gene insertion, viral infection, micro-injection, gene-gun penetration, and the combination thereof. Furthermore, the vector may further contain at least a viral or type-II RNA polymerase (Pol-II) promoter, or both, for expressing the SpRNAi-RGFP gene, a Kozak consensus translation initiation site to increase translation efficiency in eukaryotic cells, multiple SV40 polyadenylation signals downstream of the SpRNAi-RGFP gene for processing the 3'-end of the recombinant gene transcript, a pUC origin of replication for propagation in prokaryotic cells, at least two restriction/cloning sites for incorporation of the SpRNAi-RGFP gene into the vector, an optional SV40 origin for replication in mammalian cells that express the SV40 T antigen, and an optional SV40 early promoter for expressing antibiotic resistance gene in replication-competent prokaryotic cells. The expression of antibiotic resistance genes is used to serve as a selective marker for searching of successfully transfected or infected clones, possessing resistance to the antibiotics selected from the group consisted of penicillin G, ampcillin, neomycin, paromycin, kanamycin, streptomycin, erythromycin, spectromycin, phophomycin, tetracycline, rifapicin, amphotericin B, gentamicin, chloramphenicol, cephalothin, tylosin, and a combination thereof.

The SpRNAi-RGFP vector construct so obtained has been tested in a Tg(actin-GAL4:USA-gfp) strain zebrafish in vivo to target against its green EGFP gene expression. As shown in Example 3 and FIG. 3C, the liposomal transfection of an anti-EGFP pre-miRNA insert in the SpRNAi-RGFP plasmid construct (lane 4) presents a very strong EGFP gene silencing effect (>80% gene knockdown), whereas no effect can be detected in those of other inserts indicated by lanes from left to right: 1, blank vector control (Ctl); 2, pre-miRNA insert targeting HIV-p24 (mock); 3, antisense EGFP insert without the hairpin loop structure (anti); and 5, reverse pre-miRNA sequence which is completely complementary to the anti-EGFP pre-miRNA (miR*). No effect was detected on off-target genes, such as marker RGFP and house-keeping β-actin, suggesting that such intronic miRNA-mediated RNA interference (RNAi) is highly target-specific. Further, using low stringent Northern blotting analysis (FIG. 3D), we have observed the production and release of small effective intronic RNAs only from the designed SpRNAi-RGFP gene transcript (middle lane 2), but not from a natural transcript of the intron-free RGFP (left lane 1) or a transcript of a defective SpRNAi-RGFP construct without a functional 5'-splice site, while spliced RGFP exons can be linked together to form mature RNA for functional red fluorescent protein synthesis.

Evaluation of Effective Intronic MicroRNA (miRNA) Structures in vivo

The above and foregoing experiments establish the fact that intronic miRNAs provide effective means for silencing targeted gene expression in vivo. We first assess the efficacy of the intronic miRNA-mediated gene silencing and then determine the best structural designs for the intronic pre-miRNA inserts capable of inducing an optimal gene silencing effect. Based on these studies, we have learned that a strong structural preference presents in the selection of a mature miRNA strand for intracellular assembly of the RNAi-related gene silencing effector, RNA-induced gene silencing complex (RISC). RISC is a protein-RNA complex that directs either targeted gene transcript degradation or translational repression of the targeted gene transcript(s) through a RNA interference (RNAi) or post-transcriptional gene silencing (PTGS) mechanism.

In zebrafish, we have observed that the stem-loop structure of pre-miRNA determines the sequence of mature miRNA for RISC assembly, which is different from the known siRNA-associated RISC assembly (Lin et.al. (2005) *Gene* 356: 32-38). Formation of siRNA duplexes plays a key role in assembly of the siRNA-associated RISC. The two strands of the siRNA duplex are functionally asymmetric, but assembly into the RISC complex is preferential for only one strand. Such a preference is determined by the thermodynamic stability of each 5'-end base-pairing in the siRNA duplex strand. Based on this siRNA model, the formation of miRNA and its complementary miRNA (miRNA*) duplex was thought to be an essential step for the assembly of miRNA-associated RISC. If this were true, no functional bias would be observed in the stem-loop structure of a pre-miRNA. However, we observed that the stem-loop of the intronic pre-miRNA was involved in the strand selection of a mature miRNA for intracellular RISC assembly.

In experiments, we constructed anti-EGFP miRNA-expressing SpRNAi-RGFP vectors as described in Examples 1-2 and two symmetric pre-miRNAs, miRNA*-stemloop-miRNA [1] and miRNA-stemloop-miRNA* [2], were synthesized by a DNA synthesizer machine and inserted into the pre-made recombinant SpRNAi-RGFP gene vectors, respectively. Both pre-miRNA constructs contained the same double-stranded stem-arm region, which was directed against the EGFP nucleotide (nt) 280-302 sequence. Because the intronic insert site of the SpRNAi-RGFP gene is flanked with a PvuI and an MluI restriction/cloning site at its 5'- and 3'-ends, respectively, the primary insert can be easily removed and replaced by various anti-gene inserts (e.g. anti-EGFP, anti-Tyr, or anti-Hyal) possessing cohesive ends. By allowing changes in the SpRNAi insert directed against different gene transcripts, this intronic miRNA expression system provides a valuable tool for developing miRNA-associated genetic applications in vivo.

To determine the structural preference of the designed pre-miRNAs, we isolated the zebrafish small RNAs by mirVana miRNA isolation filter columns (Ambion, Austin, Tex.) and then precipitated all potential miRNA sequences complementary to the targeted EGFP by latex beads containing the target sequence. One full-length miRNA, miR-EGFP(280-302), was verified to be active in the transfections of the 5'-miRNA-stemloop-miRNA*-3' construct, as shown in FIG. 4A (gray-shading sequences). Because this effetive mature miRNA was detected only in the zebrafish transfected by the 5'-miRNA-stemloop-miRNA*-3' construct [2], the miRNA-associated RISC tended to preferably interact with the construct [2] rather than the [1] pre-miRNA structure. For visual display of the correlation between targeted gene silencing and miRNA expression (FIG. 4B), we used a Tg(actin-GAL4:UAS-gfp) strain zebrafish, which constitutively expressed a green fluorescent EGFP protein driven by a universal β-actin promoter located in almost all cells of the zebrafish, while the transfection of the anti-EGFP SpRNAi-RGFP gene vector into the zebrafish co-expressed a red fluorescent protein RGFP, serving as a positive marker indicator for miRNA generation in the affected cells. After applied the SpRNAi-RGFP vector encapsulated by a FuGene cationic liposomal reagent (Roche, Ind.) to the fish, we found that all tested vectors completely penetrated the two-week-old zebrafish larvae within 24 hours, providing fully systemic delivery of the vectors except for the scales and bones.

The marker RGFP (red) was detected in all vector-transfected zebrafish, whereas the silencing of target EGFP expression (green) was observed only in the fish transfected by the 5'-miRNA-stemloop-miRNA*-3'[2] pre-miRNA. As shown in FIG. 4C, Western blot analysis quantitatively confirmed this gene silencing result, demonstrating a >85% RGFP knockdown in the [2]-transfected zebrafish. The gene silencing effect in gastrointestinal (GI) tract area was however lower that other tissues, probably due to a high RNase activity in this area. Because the same 5'-end thermostability is applied to both anti-EGFP pre-miRNA stem-arms, we suggest that the stem-loop structure of pre-miRNA is involved in the strand selection of mature miRNA for functional RISC assembly. Given that the cleavage site of Dicer in the stem-arm is known to determine the strand selection of mature miRNA, the stem-loop of a pre-miRNA may function as a determinant for the recognition of the special cleavage site. Therefore, based the broad heterogeneity of natural stem-loop structures among various native miRNA species, we selectively used a pair of manually improved pre-mir-302 loops in these experiments, such as 5'-GCTAAGCCAGGC-3' (SEQ.ID.NO. 1) and 5'-GCCTGGCTTAGC-3' (SEQ.ID.NO.2), which have been tested to provide an optimal RISC assembly effect for the present invention.

Intronic MicroRNA-Mediated Tyrosinase and Hyaluronidase Gene Silencing in Mouse Skins Based on the above studies, we have designed and tested an optimal SpRNAi-RGFP gene construct with an either miR-Tyr or miR-Hyal pre-miRNA insert for silencing the unwanted pigmentation-related gene Tyr or aging-related gene Hyal in mouse skins. These manually designed miR-Tyr and miR-Hyal pre-miRNAs target a highly conserved region (>98% homology) in both human and mouse Tyr and Hyal genes, respectively, providing a useful animal model for testing the efficacy and safety of these optimal SpRNAi-RGFP gene constructs in skins in vivo. In nature, there are 54 native miRNAs capable of targeting human tyrosinase (Tyr; 2082 bp) for pigmentation gene silencing, including mir-1, mir-15a, mir-16, mir-31, mir-101, mir-129, mir-137, mir-143, mir-154, mir-194, mir-195, mir-196b, mir-200b, mir-200c, mir-206, mir-208, mir-214, mir-221, mir-222, mir-292-3p, mir-299-3p, mir-326, mir-328, mir-381, mir-409-5p, mir-434-5p, mir-450, mir-451, mir-452, mir-464, mir-466, mir-488, mir-490, mir-501, mir-522, mir-552, mir-553, mir-570, mir-571, mir-582, mir-600, mir-619, mir-624, mir-625, mir-633, mir-634, mir-690, mir-697, mir-704, mir-714, mir-759, mir-761, mir-768-5p, and mir-804. According to the miR target search database of the miRBase::Sequences program (http://microrna.sanger.ac.uk), all these anti-Tyr miRNAs are directed against a region within the first 300 nucleotides of the Tyr gene transcript (NCBI accession number NM000372). Moreover, there are 9 native miRNAs capable of targeting hyaluronidase (Hyal; 2518 bp; NCBI accession number NM007312) for aging gene silencing, including mir-197, mir-349, mir-434-5p, mir-549, mir-605, mir-618, mir-647, mir-680, mir-702, and mir-763. In these native miRNAs, the mir-434-5p is the only one targets both Tyr and Hyal genes in human and also it is one of the most efficient miRNAs targeting the least off-target genes other than Tyr and Hyal. However, because almost all native miRNAs have several to over fifty targets and they tend to bind with some of the target genes more strongly than others, the use of these native miRNAs is likely not specific and safe enough for the skin care purpose.

To test the feasibility of miRNA-mediated skin whitening, we have utilized the SpRNAi-RGFP expression system of the present invention to express native pre-mir-434-5p in mouse skin. As shown in FIG. 5, patched albino (white) skins of melanin-knockdown mice (W-9 black) were created by a succession of intra-cutaneous (i.c.) transduction of the pre-mir-434-5p expression vector (50 μg) directed against tyrosinase (Tyr) for 4 days (total 200 μg). The Tyr, a type-I membrane protein and copper-containing enzyme, catalyzes the critical and rate-limiting step of tyrosine hydroxylation in the biosynthesis of melanin (black pigment) in skins and hairs. Starting from about two weeks after the first i.c. injection, we observed that skin and hair melanin was significantly lost only in the pre-miRNA transfections. On the contrary, the blank control and the Pol-III (U6)-directed siRNA transfections presented no such an effect under the same dosage. Northern blot analysis using mRNAs isolated from the hair follicles of the pre-mir-434-5p transfections showed a 76.1%±5.3% reduction of Tyr expression two days post-transfection, whereas mild, non-specific degradation of random gene transcripts was detected in the siRNA-transfected skins (seen from the smearing patterns of both house-keeping control GAPDH and targeted Tyr mRNAs). Since Grimm et al. (2006) have reported that high siRNA/shRNA concentrations generated by the Pol-III-directed RNAi systems can over-saturate the cellular microRNA pathway and cause global miRNA dysregulation, this result indicates that the siRNA pathway is incompatible with the native miRNA pathway in skin tissues. Thus, the use of miRNA will likely provide a more effective, compatible and safe means for skin care. However, because the native mir-434-5p also targets five other cellular genes for silencing, including TRPS1, PITX1, LCOR, LYPLA2 and Hyal, the off-target effect of this native pre-mir-434-5p transfection remains to be determined.

In order to improve the target-specificity and safety of miRNA agents, we have re-designed the seed sequence of the mir-434-5p to form a highly matched region binding to either Tyr nucleotides 3-25 (namely miR-Tyr) or Hyal nucleotides 459-482 (namely miR-Hyal). The pre-miRNA insert sequence for Tyr gene silencing (pre-miR-Tyr) is 5'-GTCCGATCGT CGCCCTACTC TATTGCCTAA GCCGCTAAGC CAGGCGGCTT AGGCAATAGA GTAGGGCCGA CGCGTCAT-3' (SEQ.ID.NO.8), which will form a hairpin-like RNA after splicing and will be further processed into a mature miR-Tyr microRNA (miRNA) sequence containing or homologous to 5'-GCCCTACTCT ATTGCCTAAG CC-3' (SEQ.ID.NO.9). Alternatively, the pre-miRNA insert for Hyal gene silencing (pre-miR-Hyal) is 5'-GTCCGATCGT CAGCTAGACA GTCAGGGTTT GAAGCTAAGC CAGGCTTCAA ACCCTGACTG TCTAGCTCGA CGCGTCAT-3' (SEQ.ID.NO.10), which will form a different kind of hairpin-like RNA after splicing and will be further processed into a mature miR-Hyal miRNA sequence containing or homologous to 5'-AGCTAGACAG TCAGGGTTTG AA-3' (SEQ-.ID.NO. 11). Although both pre-miR-Tyr and pre-miR-Hyal constructs are re-designed based on the same mir-434-5p backbone and mir-302 stem-loop, the mature miR-Tyr and miR-Hyal so obtained are totally different from each other. As shown in FIG. 6, the transfective expressions of miR-Tyr and miR-Hyal in mouse skins specifically knock down the targeted Tyr (reduction over 90%) and Hyal genes (reduction over 67%), respectively, without any crossover off-target effect. The expression levels of mature miR-Tyr and miR-Hyal microRNAs are directly measured by Northern blot analysis, while the knockdown rates of the targeted Tyr and Hyal gene products (proteins) are determined by Western blot analysis.

Target Specificity and Safety of the miR-Tyr and miR-Hyal MicroRNA-Mediated Gene Silencing in Human Skin Cells After understanding the optimal gene silencing effects of the designed intronic miR-Tyr and miR-Hyal RNAi effectors of the present invention, we continue to test the efficacy, target specificity and safety of these SpRNAi-RGFP gene constructs with either the miR-Tyr or the miR-Hyal pre-miRNA in human skin cells and tissues for skin care. For efficient vector transfection into the human surface skin cell layers, a 1 µg/ml SpRNAi-RGFP vector solution is made by mixing 100 µg of the purified SpRNAi-RGFP vector in 1 ml of autoclaved ddH$_2$O with 99 ml of 100% DNase-free glycerin (or called glycerol). DNase-free glycerin is used to encapsulate miR-Tyr for deep skin delivery and cell membrane penetration. This forms the major ingredient base for skin whitening and lightening products. After this, more other cosmetic ingredients may be added to increase the color, fragrance, effectiveness and/or stability of the final cosmetic products. As shown in FIG. 7A, asian male arm skins treated with 2 ml of this major ingredient base expressing the aforementioned miR-Tyr (right site) versus empty SpRNAi-RGFP vector without any miRNA insert (glycerin control, left site) are compared. The result of skin whitening (loss of the black pigment-melanin) by the miR-Tyr treatment can be observed in three days after two single treatments per day, as shown in this figure.

Primary skin cell culture is then obtained by trypsin-dissociated skin explants from the tested donor with personal consent and all treatments are performed based on this consent. The vector transfection in the primary skin culture is performed as described in Examples 3 and 6 (total 60 µg). FIG. 7B shows that Western blot analyses of the loss of the targeted tyrosinase proteins and its substrate melanin are biostatistically significant (p>0.001). The reduction amounts of tyrosinase proteins and its substrate melanin in skins is proportional to the treated concentrations of the miR-Tyr expression vector, indicating the positive correlation between the increase of the miR-Tyr treatment and the loss of the targeted tyrosinase proteins and its substrate melanin. No effect is found in other treatments, such as an empty SpRNAi-RGFP vector without any miRNA insert (glycerin) and an SpRNAi-RGFP vector expressing an anti-EGFP pre-miRNA insert (miR-gfp). At the concentration of 1 µg/ml of the miR-Tyr expression vector transfection, the maximal Tyr gene silencing rate is approximately 55%-60% for tyrosinases and 30%-45% for melanin, while the expression of non-target house-keeping control β-actin is not affected by the miR-Tyr treatment, indicating the high target-specificity of this man-made microRNA molecule. FIG. 7C further shows that the skin melanin levels are significantly reduced as shown in bright-field (BF) photographs of the primary skin cell culture (upper panels), while melanin (black dots around the cell nuclei) is highly expressed in the normal skin cells without the miR-Tyr treatment (i.e. blank and glycerin only). The miR-Tyr-treated skin cells present very limited melanin accumulation, demonstrating an effective skin-whitening effect in vivo. In regard to this loss of skin melanin, the targeted tyrosinase expression is concurrently reduced in the miR-Tyr-treated skin cells, as determined by immunocytochemical (ICC) staining analysis (FIG. 7C, lower panels). Therefore, based on the overall results of FIG. 7A-FIG. 7C, the designed miR-Tyr microRNA can be used to knock down the tyrosinase expression and thus successfully blocks melanin production in the human skins in vivo.

After the gene silencing efficacy of the miR-Tyr is established in human skins, we use gene microarray analysis (GeneChip U133A&B arrays, Affymetrix, Santa Clara, Calif.) to assess the changes of over 32,668 human gene expression in the above miR-Tyr-transfected versus non-treated primary skin cell cultures, showing a much more target-specific and less off-target gene silencing effect than the use of native mir-434. Total RNAs from each tested cell culture is isolated using RNeasy spin columns (Qiagen, Valencia, Calif.). As shown in FIG. 8A (left), the result of microarray analysis in non-treated (miR−) versus miR-Tyr-transfected (miR+) primary skin cell cultures shows that there are only two genes altered more than 1.5 fold (>50% change of gene expression), including the targeted tyrosinase (Tyr) and its associated TRP1 gene (FIG. 8B), indicating that the miR-Tyr-mediated gene silencing effect is highly specific to the targeted Tyr. Furthermore, no genes related to cytotoxicity or interferon-mediated PKR/2-5A pathways are affected, suggesting that this gene silencing effect is safe for skin care treatments (FIG. 8B). We have also used Northern blot analysis to compare and assess the gene expression levels of these microarray-identified genes (FIG. 8C), confirming the same result of FIG. 8A and FIG. 8B. In further comparison with the result of the native mir-434-5p transfection (FIG. 8A, right), the rate of correlation coefficient (CC) clearly presents a high 99.8% of the 32,668 gene expression remained to be unchanged in the miR-Tyr-transfected (miR+) cells, while a low 77.6% CC rate is found in the mir-434-5p-transfected cells. This means that the expression patterns of only 65 cellular genes are altered by the designed miR-Tyr transfection, whereas those of over 7,317 genes are changed by the native mir-434-5p transfection. Because it is a well-known fact that almost all native microRNAs (miRNAs) target multiple cellular genes due to their mismatched stem-arms, our present invention demonstrates that the re-design of these stem-arm regions is required for the safe use of these miRNAs in target-specific gene silencing applications.

Thus, utilization of intronic hairpin-like microRNA (miRNA)/shRNA expression vectors of the present invention provides a powerful new strategy for skin care in vivo, particularly for hyperpigmentation treatment and aging prevention. Under the same treatment, Pol-II-transcribed intronic miRNAs do not cause any detectable cytotoxicity, whereas Pol-III-directed siRNAs induced non-specific mRNA degradation as previously reported (Sledz et.al. supra; Lin (2004b) supra). This underscores the fact that intronic miRNA is effective and target-specific in vivo without any potential cytotoxic effect of the double-stranded siRNAs. Because such an intronic miRNA-mediated gene silencing pathway is well coordinated by multiple intracellular regulation systems, including Pol-II transcription, RNA splicing and NMD processing, the gene silencing effect of intronic miRNA is considered to be most effective, specific and safe in all three currently known RNAi pathways. Advantageously overall, the use of re-designed intronic miRNAs offers a relatively long-term, effective, specific and safe gene manipulation approach for skin care applications, preventing the unspecific off-target gene silencing cytotoxicity as shown in the conventional siRNA methods.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide.

Oligonucleotide: a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Nucleic Acid: a polymer of nucleotides, either single or double stranded.

Nucleotide Analog: a purine or pyrimidine nucleotide that differs structurally from A, T, G, C, or U, but is sufficiently similar to substitute for the normal nucleotide in a nucleic acid molecule.

Gene: a nucleic acid whose nucleotide sequence codes for an RNA and/or a polypeptide (protein). A gene can be either RNA or DNA.

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding.

Precursor messenger RNA (pre-mRNA): primary ribonucleotide transcripts of a gene, which are produced by type-II RNA polymerase (Pol-II) machineries in eukaryotes through an intracellular mechanism termed transcription. A pre-mRNA sequence contains a 5'-end untranslated region, a 3'-end untranslated region, exons and introns.

Intron: a part or parts of a gene transcript sequence encoding non-protein-reading frames.

Exon: a part or parts of a gene transcript sequence encoding protein-reading frames.

Messenger RNA (mRNA): assembly of pre-mRNA exons, which is formed after intron removal by intranuclear spliceosomal machineries and served as a protein-coding RNA for protein synthesis.

cDNA: a single stranded DNA that is complementary to an mRNA sequence and does not contain any intronic sequences.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Complementary or Complementarity or Complementation: used in reference to polynucleotides (i.e. a sequence of nucleotides) related by the base-pairing rules. For example, the sequence "A-G-T" is complementary to the sequence "T-C-A," and also to "T-C-U." Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Homologous or Homology: refers to a polynucleotide sequence having similarities with a gene or mRNA sequence. A nucleic acid sequence may be partially or completely homologous to a particular gene or mRNA sequence, for example. Homology may also be expressed as a percentage determined by the number of similar nucleotides over the total number of nucleotides.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

RNA interference (RNAi): a posttranscriptional gene silencing mechanism in eukaryotes, which can be triggered by small RNA molecules such as microRNA and small interfering RNA. These small RNA molecules usually function as gene silencers, interfering with expression of intracellular genes containing either completely or partially complementarity to the small RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Pre-miRNA: hairpin-like single-stranded RNAs containing stem-arm and stem-loop regions for interacting with intracellular RNaseIII endoribonucleases to produce one or multiple microRNAs capable of silencing a targeted gene or genes complemetary to the microRNA sequence(s). The stem-arms of a pre-miRNA can form either perfectly (100%) or partially (mismatched) hybridized duplex conformation, while the stem-loop connects one end of the stem-arm duplex to form a circle or hairpin-loop conformation.

Small interfering RNA (siRNA): short double-stranded RNAs sized about 18-25 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid molecule such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and/or expression of nucleic acids to which they are linked. Vectors capable of directing the expression of genes encoding for one or more polypeptides are referred to herein as "expression vectors". Particularly important vectors allow cloning of cDNA from mRNAs produced using a reverse transcriptase.

Cistron: a sequence of nucleotides in a DNA molecule coding for an amino acid residue sequence and including upstream and downstream DNA expression control elements.

Promoter: a nucleic acid to which a polymerase molecule recognizes, perhaps binds to, and initiates synthesis. For the purposes of the instant invention, a promoter can be a known polymerase binding site, an enhancer and the like, any sequence that can initiate synthesis by a desired polymerase.

Antibody: a peptide or protein molecule having a pre-selected conserved domain structure coding for a receptor capable of binding a pre-selected ligand.

B. Compositions

A recombinant nucleic acid composition for inducing of RNA splicing- and/or processing-associated gene silencing comprises:
  a) At least an intron, wherein said intron is flanked with a plurality of exons and can be cleaved out of the exons by intracellular RNA splicing and/or processing machineries; and
  b) A plurality of exons, wherein said exons can be linked to form a gene possessing a desired function.

The above recombinant nucleic acid composition, further comprises:
  a) At least a restriction/cloning site, wherein said restriction/cloning site is used for incorporating the recombinant nucleic acid composition into an expression-competent vector for expressing the primary RNA transcripts of said recombinant nucleic acid composition in skin cells; and
  b) A plurality of transcription and translation termination sites, wherein said transcription and translation termination sites are used to produce the correct sizes of the RNA transcripts of the recombinant nucleic acid composition.

The intron of the above recombinant nucleic acid composition, further comprises:
  a) A gene-silencing effector insert complementary or homologous to a targeted gene;
  b) A 5'-donor splice site;
  c) A 3'-acceptor splice site;
  d) A branch point motif for spliceosomal recognition;
  e) A poly-pyrimidine tract for spliceosomal interaction; and
  f) A plurality of linkers for connection of the above major components.

The 5'-donor splice site is a nucleotide sequence containing or homologous to either 5'-GTAAGAGK-3' (SEQ.ID.NO.3) or GU(A/G)AGU motifs (such as 5'-GTAAGAGGAT-3' (SEQ ID NO: 27), 5'-GTAAGAGT-3', 5 -GTAGAGT-3' and 5'-GTAAGT-3'), while the 3' -acceptor splice site is a nucleotide sequence containing or homologous to either GWKSCYRCAG (SEQ.ID.NO.4) or CT(A/G)A(C/T)NG motifs (such as 5'-GATATCCTGC AG-3' (SEQ ID NO: 28), 5'-GGCTGCAG-3' and 5'-CCACAG-3'). Moreover, a branch point sequence is located between the 5'- and 3'-splice sites, containing homology to 5' -TACTWAY-3' (SEQ.ID.NO.5) motifs, such as 5'-TACTAAC-3' and 5'-TACTTAT-3'. The adenosine "A" nucleotide of the branch-point sequence forms a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ.ID.NO.6) or 5 '-(TC)nNCTAG(G/-)-3 ' (SEQ.ID.NO.7) motifs. The symbols of "m" and "n" indicate multiple repeats ≥1; most preferably, the m number is equal to 1~3 and the n number is equal to 7~12. The symbol "-" refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)."For all of the above spliceosomal recognition components, the deoxythymidine (T) nucleotide is replaceable with uridine (U).

C. Methods

An in vivo method for inducing RNA splicing- and processing-associated gene silencing effects in human skin cells, comprising the steps of:
  a) Constructing a recombinant nucleic acid composition that contains a spliceosomal intron encoding a gene-silencing effector flanked with exons, wherein said intron encodes a hairpin-like RNA structure, which can be cleaved out of the exons for inducing RNA-mediated gene silencing;
  b) Cloning said recombinant nucleic acid composition into an expression-competent vector; and
  c) Introducing said vector into a plurality of skin cells in vivo, wherein said skin cells generate a plurality of primary RNA transcripts of said recombinant nucleic acid composition, and wherein the skin cells splice the intron from the primary RNA transcripts so as to provide gene-silencing effects against a gene containing sequence homologous or complementary to the gene-silencing effector and the exons may be linked together to encode a protein.

EXAMPLES

The following examples serve to illustrate certain preferred embodiments and aspects of the present invention and are not to be construed as limiting the scope thereof.

In the experimental disclosure which follows, the following abbreviations apply: M (molar); mM (millimolar); μm (micromolar); mol (moles); pmol (picomolar); gm (grams); mg (milligrams) μg (micrograms); ng (nanograms); L (liters); ml (milliliters); μl (microliters); ° C. (degrees Centigrade); cDNA (copy or complementary DNA); DNA (deoxyribonucleic acid); ssDNA (single stranded DNA); dsDNA (double-stranded DNA); dNTP (deoxyribonucleotide triphosphate); RNA (ribonucleic acid); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); and ATCC (American Type Culture Collection, Rockville, Md.).

Example 1

Construction of SPRNAi-Containing Recombinant Gene (SpRNAi-RGFP)

Synthetic nucleic acid sequences used for generation of three different SpRNAi introns containing either sense-, antisense- or hairpin-EGFP insert were listed as follows: N1-sense, 5'-pGTAAGAGGAT CCGATCGCAG GAGCG-CACCA TCTTCTTCAA GA-3' (SEQ.ID.NO. 12); N1-antisense, 5'-pCGCGTCTTGA AGAAGATGGT GCGCTC-CTGC GATCGGATCC TCTTAC-3' (SEQ.ID.NO.13); N2-sense, 5'-pGTAAGAGGAT CCGATCGCTT GAAGAAGATG GTGCGCTCCT GA-3' (SEQ.ID.NO.14); N2-antisense, 5'-pCGCGTCAGGA GCGCACCATC TTCT-TCAAGC GATCGGATCC TCTTAC-3' (SEQ.ID.NO.15); N3-sense, 5'-pGTAAGAGGAT CCGATCGCAG GAGCG-CACCA TCTTCTTCAA GTTAACTTGA AGAAGATGGT GCGCTCCTGA-3' (SEQ.ID.NO.16); N3-antisense, 5'-pCGCGTCAGGA GCGCACCATC TTCTTCAAGT TAACTTGAAG AAGATGGTGC GCTCCTGCGA TCG-GATCCTC TTAC-3' (SEQ.ID.NO.17); N4-sense, 5'-pCGCGTTACTA ACTGGTACCT CTTCTTTTTT TTTTTGATAT CCTGCAG-3' (SEQ.ID.NO.18); N4-antisense, 5'-pGTCCTGCAGG ATATCAAAAA AAAAAGAAGA GGTACCAGTT AGTAA-3' (SEQ.ID.NO.19). In addition, two exon fragments were generated by DraII restriction enzyme cleavage of a red fluorescent RGFP gene (SEQ.ID.NO.20) at its 208th nucleotide (nt) site and the 5' fragment was further blunt-ended by T4 DNA polymerase. The RGFP referred to a new red-shifted fluorescent chromoprotein gene generated by insertion of an additional aspartate at the 69th amino acid (a.a.) site of HcRed1 chromoproteins from *Heteractis crispa*. (BD Biosciences, Calif.), developing less aggregate and almost twice intense far-red fluorescent emission at the 570-nm wavelength. We also cleaved a pHcRed1-N1/1 plasmid (BD Biosciences, Calif.) with XhoI and XbaI restriction enzymes and purified a full 769-bp RGFP gene fragment and a 3,934-bp empty plasmid separately isolated from 2% agarose gel electrophoresis.

Hybridization of N1-sense to N1-antisense, N2-sense to N2-antisense, N3-sense to N3-antisense and N4-sense to N4-antisense was separately performed by heating each complementary mixture of sense and antisense (1:1) sequences to 94° C. for 2 min and then 70° C. for 10 min in 1×PCR buffer (e.g. 50 mM Tris-HCl, pH 9.2 at 25° C., 16 mM (NH$_4$)$_2$SO$_4$, 1.75 mM MgCl$_2$). Continuously, sequential ligation of either N1, N2 or N3 hybrid to the N4 hybrid was performed by gradually cooling the mixture of N1-N4, N2-N4 or N3-N4 (1:1) hybrids respectively from 50° C. to 10° C. over a period of 1 hr, and then T$_4$ ligase and relative buffer (Roche, Ind.) were mixed with the mixture for 12 hr at 12° C., so as to obtain introns for insertion into exons with proper ends. After the RGFP exon fragments were added into the reaction (1:1:1), T4 ligase and buffer were adjusted accordingly to reiterate ligation for another 12 hr at 12° C. For cloning the right sized recombinant RGFP gene, 10 ng of the ligated nucleotide sequences were amplified by PCR with a pair of RGFP-specific primers 5'-CTCGAGCATG GTGAGCGGCC TGCTGAA-3 ' (SEQ.ID.NO.21) and 5'-TCTAGAAGTT GGCCTTCTCG GGCAGGT-3' (SEQ.ID.NO.22) at 94° C., 1 min, 52°, 1 min and then 68° C., 2 min for 30 cycles. The resulting PCR products were fractionated on a 2% agarose gel, and a ~900-bp nucleotide sequences was extracted and purified by a Gel Extraction kit (Qiagen, Calif.). The composition of this ~900 bp SpRNAi-containing RGFP gene was further confirmed by sequencing.

Because the recombinant gene possessed an XhoI and an XbaI restriction site at its 5'- and 3'-end, respectively, it can be easily cloned into a vector with cohesive ends to the XhoI and XbaI cloning sites. The vector must be a skin-compatible, expressing-competent organism or suborganism selected from the group consisted of plasmids, cosmids, phagmids, yeast artificial chromosomes, jumping genes, transposons and viral vectors. Moreover, because the insert within the intron is also flanked with a PvuI and an MluI restriction site at its 5'- and 3'-end, respectively, we can remove and replace the insert with another different insert sequence possessing cohesive ends to the PvuI and MluI cloning sites. The inserted sequence is preferably a hairpin-like gene silencing effector containing high complementarity to a gene target selected from the group consisted of fluorescent protein (GFP) genes, luciferase genes, lac-Z genes, viral genes, bacterial genes, plant genes, animal genes and human genes. The complementarity and/or homology rate between the gene-silencing effector insert and its targeted gene is ranged from about 30%-100%, more preferably 35%-49% for a hairpin-shRNA insert and 90%-100% for both sense-stRNA and antisense-siRNA inserts.

Example 2

Cloning of SpRNAi-Containing Genes into A Expression-Competent Vector

Because the recombinant SpRNAi-RGFP gene possessed an XhoI and an XbaI restriction site at its 5'- and 3'-end, respectively, it can be easily cloned into a vector with relatively cohesive ends to the XhoI and XbaI restriction sites. We mixed the SpRNAi-RGFP gene with the linearized 3,934-bp empty pHcRed1-N1/1 plasmid at 1:16 (w/w) ratio, cooled the mixture from 65° C. to 15° C. over a period of 50 min, and then added $T_4$ ligase and relative buffer accordingly into the mixture for ligation at 12° C. for 12 hr. This formed an SpRNAi-RGFP expression vector, which can be propagated in an *E.coli* DH5α LB culture containing 50 µg/ml kanamycin (Sigma Chemical, St. Louis, Mo.). A positive clone was confirmed by PCR with the RGFP-specific primers SEQ.ID.NO.21 and SEQ.ID.NO.22 at 94° C., 1 min and then 68° C., 2 min for 30 cycles, and for further sequencing. For cloning into viral vectors, the same ligation procedure could be performed except using an XhoI/XbaI-linearized pLNCX2 retroviral vector (BD) instead. Since the insert within the SpRNAi intron was flanked with a PvuI and a MluI restriction site at its 5'- and 3'-end, respectively, we could remove and replace the anti-EGFP shRNA insert with the miR-Tyr or miR-Hyal insert sequences possessing cohesive ends to the PvuI and MluI cloning sites.

Synthetic nucleic acid sequences used for generation of various SpRNAi introns containing either miR-Tyr or miR-Hyal insert were listed as follows: miR-Tyr-sense, 5'-GTC-CGATCGT CGCCCTACTC TATTGCCTAA GCCGCTAAGC CAGGCGGCTT AGGCAATAGA GTAGGGCCGA CGCGTCAT-3' (SEQ.ID.NO.8); miR-Tyr-antisense, 5'-ATGACGCGTC GGCCCTACTC TATTGC-CTAA GCCGCCTGGC TTAGCGGCTT AGGCAATAGA GTAGGGCGAC GATCGGAC-3' (SEQ.ID.NO.23); and miR-Hyal-sense, 5'-GTCCGATCGT CAGCTAGACA GTCAGGGTTT GAAGCTAAGC CAGGCTTCAA ACCCTGACTG TCTAGCTCGA CGCGTCAT-3' (SEQ.ID.NO.10); miR-Hyal-antisense, 5'-ATGACGCGTC GAGCTAGACA GTCAGGGTTT GAAGCCTGGC TTAGCTTCAA ACCCTGACTG TCTAGCTGAC GATCGGAC-3' (SEQ.ID.NO.24). The inserts were formed by hybridization of miR-Tyr-sense to miR-Tyr-antisense and miR-Hyal-sense to miR-Hyal-antisense, respectively. These miR-Tyr- and miR-Hyal-expressing vectors so obtained could be propagated in *E.coli* DH5α LB-culture containing either 50 µg/ml kanamycin (for pHcRed1-N1/1 plasmid-based vector) or 100 82 g/ml ampicillin (for pLNCX2 viral vector). The propagated SpRNAi-RGFP vectors could be isolated and purified using a Mini-prep or Maxi-prep Plasmid Extraction kit (Qiagen, Calif.), following the manufacturer's suggestion. For pLNCX2 vectors, we could also use a packaging cell line PT67 (BD) for producing infectious but replication-incompetent virus. The transfected PT67 cells were grown in 1× DMEM medium supplemented with 10% fetal bovine serum with 4 mM L-glutamine, 1 mM sodium pyruvate, 100 µg/ml streptomycin sulfate and 50 µg/ml neomycin (Sigma Chemical, MO) at 37° C. under 5% $CO_2$. The titer of virus produced by PT67 cells was determined to be at least $10^6$ cfu/ml before transfection.

Example 3

In Vivo Vector Transfection

For vector transfection into cell cultures, fish larvae and mouse skins, we first mixed the SpRNAi-RGFP expression plasmid vectors containing either anti-EGFP, miR-Tyr or miR-Hyal pre-miRNA insert with a FuGene reagent (Roche, Ind.), following the manufacturer's suggestion. Then, the mixtures were directly applied to the cell cultures (i.e. primary human skin culture), fish larvae or mouse skins, respectively. Vectors containing an insert-free RGFP gene and an SpRNAi-RGFP gene with a pre-miRNA insert against the HIV gag-p24 gene were used as negative controls. Tissue or cell morphology and fluorescence imaging was photographed at 0-, 24-, 48-, and 72-hr time points after the first transfection. For transfection to the human skins in vivo, a pre-made SpRNAi-RGFP vector solution was formed by mixing certain amounts (i.e. 1-1000 µg) of the purified SpRNAi-RGFP vector with or without either anti-EGFP, miR-Tyr or miR-Hyal pre-miRNA insert in 1 ml of autoclaved dd$H_2$O with 99 ml of 100% DNase-free glycerin (or glycerol). Then, this solution was directly applied to the skins with gentle massage for 3 min.

Example 4

Northern Blot Analysis

RNA (20 µg total RNA or 2 µg poly[$A^+$] RNA) was fractionated on 1% formaldehyde-agarose gels and transferred onto nylon membranes (Schleicher & Schuell, Keene, N. H.). Synthetic probes complementary to either the 75-bp junction sequence flanking between the RGFP 5'-exon and the anti-EGFP pre-miRNA insert or miR-Tyr (SEQ.ID.NO.9), or miR-Hyal (SEqID.NO.10), were labeled with the Prime-It II kit (Stratagene, La Jolla, Calif.) by random primer extension in the presence of [$^{32}$P]-dATP (>3000 Ci/mM, Amersham International, Arlington Heights, Ill.), and purified with 10 bp-cutoff Micro Bio-Spin chromatography columns (Bio-Rad, Hercules, Calif.). Hybridization was carried out in the mixture of 50% freshly deionized formamide (pH 7.0), 5×Denhardt's solution, 0.5% SDS, 4×SSPE and 250 mg/mL denatured salmon sperm DNA fragments (18 hr, 42° C.). Membranes were sequentially washed twice in 2×SSC, 0.1% SDS (15 min, 25° C.), and once in 0.2×SSC, 0.1% SDS (45 min, 37° C.) before autoradiography.

Example 5

SDS-PAGE and Western Blot Analysis

For immunoblotting of targeted proteins, isolated cells were rinsed with ice cold PBS after growth medium was removed, and then treated with the CelLytic-M lysis/extraction reagent (Sigma, Mo.) supplemented with protease inhibitors, Leupeptin, TLCK, TAME and PMSF, following manufacture's recommendations. The cells were incubated at room temperature on a shaker for 15 min, scraped into microtubes, and centrifuged for 5 min at 12,000×g to pellet the cell debris. Protein-containing cell lysate were collected and stored at −70° C. until use. Protein determinations were measured with SOFTmax software package on an E-max microplate reader (Molecular Devices, Sunnyvale, Calif.). Each 30 µg cell lysate was added into SDS-PAGE sample buffer either with (reduced) or without (unreduced) 50 mM DTT, and boiled for 3 min before loaded onto 8% polyacylamide gels, while the reference lane was loaded with 2~3 µl molecular weight markers (Bio-Rad). SDS-polyacrylamide gel electrophoresis was performed according to the standard protocols (Molecular Cloning, 3rd ED). Protein fractionations were electroblotted onto a nitrocellulose membrane, blocked with Odyssey blocking reagent (Li-Cor Biosciences, Lincoln, NB) for 1~2 hr at the room temperature. We then assessed protein expression using primary antibodies directed against either EGFP (1:5,000; JL-8, BD), RGFP (1:10,000; BD), Tyr (1:2,000; Santa Crutz), or Hyal (1:2,000; Santa Crutz), overnight at 4° C. The protein blots were then rinsed 3 times with TBS-T and exposed to a secondary antibody, goat anti-mouse IgG conjugate with Alexa Fluor 680 reactive dye (1:2,000; Molecular Probes), for 1 hr at the room temperature. After three more TBS-T rinses, scanning and image analysis were completed with Li-Cor Odyssey Infrared Imager and Odyssey Software v.10 (Li-Cor).

Example 6

Intronic RNA-mediated Gene Silencing in Zebrafish

Tg(actin-GAL4:UAS-gfp) strain zebrafish larvae were raised in a fish container with 10 ml of 0.2× serum-free RPMI 1640 medium during transfection. A transfection pre-mix was prepared by gently dissolving 60 µl of a FuGene liposomal transfection reagent (Roche Biochemicals, Indianapolis, Ind.) in 1 ml of 1× serum-free RPMI 1640 medium. The SpRNAi-RGFP vectors (20 µg) with or without an anti-EGFP pre-miRNA insert, as described in Examples 1-2, were then mixed with the pre-mix solution, stayed on ice for 30 min and directly applied to the Tg(actin-GAL4:UAS-gfp) fish in the container. Total three dosages were given in a 12 hr interval (total 60 µg). Samples were collected 60 hr after the first transfection.

Example 7

Intronic mir-434-5p and miR-Tyr-Mediated Gene Silencing in Mouse Skins in vivo

Patched albino (white) skins of melanin-knockdown mice (W-9 black strain) were created either by a succession of intra-cutaneous (i.c.) injection of an isolated SpRNAi-RGFP gene expression vector with the native mir-434-5p pre-miRNA insert for 4 days (total 200 µg) or by a direct skin infusion of a liposome-encapsulated SpRNAi-RGFP gene expression vector with the designed miR-Tyr pre-miRNA insert for two times per day for six days (total 240 µg). For generation of the SpRNAi-RGFP gene expression vector with the native mir-434-5p pre-miRNA insert, we followed the same procedure as described in Example 2, except using a synthetic mir-434-5p pre-miRNA for intronic insertion (i.e. 5'-GTCCGATCGT CUCGACUCUG GGUUUGAACC AAAGCUCGAC UCAUGGUUUG AACCAUUACU UAAUUCGUGG UUUGAACCAU CACUCGACUC CUGGUUCGAA CCAUCCGACG CGTCAT-3' (SEQ.ID.NO.25)). For efficient delivery into target tissues, the construct was mixed with a FuGene liposomal transfection reagent (Roche, Ind.), following a similar protocol as described in Examples 3 and 6.

Example 8

Intronic miR-Tyr-Mediated Gene Silencing in Human Skins

For efficient vector transfection into the human multiple skin cell layers, a 1 µg/ml SpRNAi-RGFP vector solution is made by mixing 100 µg of the purified SpRNAi-RGFP vector in 1 ml of autoclaved ddH$_2$O with 99 ml of 100% DNase-free glycerin (or called glycerol). DNase-free glycerin is used to encapsulate miR-Tyr for deep skin delivery and cell membrane penetration. This forms the major ingredient base for our present skin whitening and lightening inventions. Then, one (heft arm) of the inventor's arm skins was directly treated with one 2 ml of this major ingredient base solution expressing the designed miR-Tyr on the right site and another 2 ml of the empty SpRNAi-RGFP vector without any miRNA insert on the left site, as compared. The result of skin whitening (loss of the black pigment-melanin) by the miR-Tyr treatment was observed three days after two single treatments per day.

Example 9

Immunocytochemical (ICC) Staining Assay

An immunochemical staining kit was obtained from Imgenex (San Diego, Calif.) and used according to the manufacturer's suggestion. The specimens were first rinsed in PBS three times and incubated with Zeller's solution (10 mM Tris, 100 mM MgCl$_2$, 5% fetal calf serum, 1% BSA and 0.5% Tween-20, pH 7.4) for 30 min. Then the specimens were incubated with primary antibody (diluted in Zeller's solution) overnight in a humidified chamber at 4° C. After that, the specimens were washed with TBST three times and incubated with secondary antibody for 2 hr, using biotinylated goat anti-rabbit or horse anti-mouse antibody as the secondary antibody (Chemicon, Temecula, Calif.). Then, we washed the specimens once with TBST and used streptavidin-HRP as the tertiary antibody for another 2 hr. Then, the specimens were washed with PBT once and the bound antibody was detected with the DAB substrates. Positive results were observed under a 100× microscope with whole field scanning and recorded at 100× and 400× magnification (TE2000 inverted microscopic quantitation system).

Example 10

Microarray Analysis

To prepare labeled probes for microarray hybridization, the extracted total RNAs (2 µg) were converted into double-stranded cDNAs, using a Superscript Choice system kit (Gibco/BRL, Gaithersburg, MD) with a modified oligo(dT)$_{24}$-T7 promoter primer, such as 5'-GGCCAGT-GAA TTGTAATACG ACTCACTATA GGGAGGCGG-(dT)$_{24}$-3' (SEQ ID NO: 33), following the manufacturer's protocol. Double-stranded cDNAs were purified by phenol/chloroform extractions, precipitated with ethanol, and resuspended at a concentration of 0.5 µg/µl in diethyl pyrocarbonate (DEPC)-treated ddH$_2$O. Phase-Lock Gel (5'Prime →3'Prime, Inc., Boulder, Colo.) was used for all organic extractions to increase recovery. In-vitro transcription was performed with T7 RNA polymerase and with 1 µg of cDNA, 7.5 mM unlabeled ATP and GTP, 5 mM unlabeled UTP and CTP, and 2 mM biotin-labeled CTP and UTP (biotin-11-CTP, biotin-16-UTP, Enzo Diagnostics). Reactions were carried out for 4 hr at 37° C., and cRNA was purified by RNeasy spin columns (Qiagen, Calif.). A sample was separated on a 1% agarose gel to check the size range, and then µg of cRNA was fragmented randomly to an average size of 50 bases by heating at 94° C. for 35 min in 40 mM Tris-acetate, pH 8.0, 100 mM KOAc/30 mM MgOAc.

A set of four oligonucleotide microarrays (GeneChip U133A&B arrays, Affymetrix, Santa Clara, Calif.) containing total 32,668 genes were used for hybridization. Hybridizations were completed in 200 µl of AFFY buffer (Affymetrix) at 40° C. for 16 hr with constant mixing. After hybridization, arrays were rinsed three times with 200 µl of 6× SSPE-T buffer (1× 0.25 M sodium chloride/15 mM sodium phosphate, pH 7.6/1 mM EDTA/0.005% Triton) and then washed with 200 µl of 6× SSPE-T for 1 hr at 50° C. The arrays were rinsed twice with 0.5× SSPE-T and washed with 0.5× SSPE-T at 50° C. for 15 min. Staining was done with 2 µg/ml streptavidin-phycoerythrin (Molecular Probes) and 1 mg/ml acetylated BSA (Sigma) in 6× SSPE-T (pH 7.6). The arrays were read at 7.5 µm with a confocal scanner (Molecular Dynamics) and analyzed with Affymetrix Microarray Suite version 4.0 software. The samples were normalized by using the total average difference between perfectly matched probe and the mismatched probe. The differential signals that were induced greater than 2-fold are collected.

Example 11

Statistical Analysis

Results were presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ were considered significant. All p values were determined from two-tailed tests.

It is understood that the examples and embodiments described herein are for illustrative purposes only and that various modifications or changes in light thereof will be suggested to persons skilled in the art, and are to be included within the spirit and purview of the invention as set forth in the appended claims. All publications and patents cited herein are incorporated herein by reference in their entirety for all purposes.

REFERENCES

The following references are hereby incorporated by reference as if fully set forth herein:
1. Fire et al. (1998) Potent and specific genetic interference by double-stranded RNA in Caenorhabditis elegans. *Nature* 391: 806-811.
2. Elbashir et.al. (2001) Duplexes of 21-nucleotide RNAs mediate RNA interference in cultured mammalian cells. *Nature* 411: 494-498.
3. Lin et.al. (2001) A Novel mRNA-cDNA interference phenomenon for silencing bcl-2 expression in human LNCaP cells. *Biochem. Biophys. Res. Commun.* 281: 639-644.
4. Grant S. R. (1999) Dissecting the mechanisms of posttranscriptional gene silencing: divide and conquer. *Cell* 96: 303-306.
5. Lin et. al (2001) D-RNAi (messenger RNA-antisense DNA interference) as a novel defense system against cancer and viral infections. *Current Cancer Drug Targets* 1: 241-247.
6. Bartel D. P. (2004) MicroRNAs: genomics, biogenesis, mechanism, and function. *Cell* 116: 281-297.
7. Lin et.al. (2004a) Novel RNAi therapy—Intron-derived microRNA drugs. *Drug Design Reviews* 1: 247-255.
8. Stark et.al. (1998) How cells respond to interferons. *Annu. Rev. Biochem.* 67: 227-264.
9. Brantl S. (2002) Antisense-RNA regulation and RNA interference. *Biochimica et Biophysica Acta* 1575: 15-25.
10. Jen et.al. (2000) *Stem Cells* 18: 307-319.
11. Ying et.al. (1999) Suppression of activin-induced apoptosis by novel antisense strategy in human prostate cancer cells. *Biochem. Biophys. Res. Commun.* 265: 669-673.
12. Tuschl T. (2002) Expanding small RNA interference. *Nat Biotechnol.* 20: 446-448.
13. Miyagishi M, Taira K. (2002) U6 promoter-driven siRNAs with four uridine 3' overhangs efficiently suppress targeted gene expression in mammalian cells. *Nat Biotechnol* 20: 497-500.
14. Lee N S, Dohjima T, Bauer G, Li H, Li M J, Ehsani A, Salvaterra P, Rossi J. (2002) Expression of small interfering RNAs targeted against HIV-1 rev transcripts in human cells. *Nat Biotechnol* 20: 500-505.
15. Paul C P, Good P D, Winer I, Engelke D R. (2002) Effective expression of small interfering RNA in human cells. *Nat Biotechnol* 20: 505-508.
16. Gunnery S, Ma Y, Mathews M B. (1999) Termination sequence requirements vary among genes transcribed by RNA polymerase III. *J Mol Biol.* 286: 745-757.
17. Schramm L, Hernandez N. (2002) Recruitment of RNA polymerase III to its target promoters. *Genes Dev.* 16: 2593-2620.
18. Sledz, C A, Holko M, de Veer M J, Silverman R H, Williams B R. (2003) Activation of the interferon system by short-interfering RNAs. *Nat Cell Biol.* 5: 834-839.
19. Lin S L, Ying S Y. (2004b) Combinational therapy for HIV-1 eradication and vaccination. *Intrn'l J Oncol.* 24: 81-88.
20. Grimm D, Streetz K L, Jopling C L, Storm T A, Pandey K, Davis C R, Marion P, Salazar F, Kay M A. (2006) Fatality in mice due to oversaturation of cellular microRNA/short hairpin RNA pathways. *Nature* 441: 537-541.
21. Nott et al. (2003) *RNA* 9: 607-617.
22. Clement et.al. (1999) *RNA* 5: 206-220.
23. Lin S L, Chang D, Wu D Y, Ying S Y. (2003) A novel RNA splicing-mediated gene silencing mechanism potential for genome evolution. *Biochem Biophys Res Commun.* 310: 754-760.
24. Lin et.al. (2005) Asymmetry of intronic pre-microRNA structures in functional RISC assembly. *Gene* 356: 32-38.
25. Ying et.al. (2004) Intron-derived microRNAs—fine tuning of gene functions. *Gene* 342: 25-28.

26. Ying et.al. (2005) Intronic microRNAs. *Biochem Biophys Res Commun.* 326: 515-520.
27. Zhang G., Taneja K L, Singer R H, Green M R. (1994) Localization of pre-mRNA splicing in mammalian nuclei. *Nature* 372: 809-812.
28. Lewis B P, Green R E, Brenner S E. (2003) Evidence for the widespread coupling of alternative splicing and nonsense-mediated mRNA decay in humans. *Proc. Natl. Acad. Sci. USA* 100: 189-192.
29. Ghosh S, Garcia-Blanco M A. (2000) Coupled in vitro synthesis and splicing of RNA polymerase II transcripts. *RNA* 6: 1325-1334.
30. Tang, G. (2005) *Trends Biochem Sci.* 30: 106-114.
31. Lin et al. (2008) Intron-mediated RNA interference and microRNA (miRNA). *Frontiers in Bioscience* 13: 2216-2230.
32. Lin S L, Ying S Y. (2006a) Gene silencing in vitro and in vivo using intronic microRNAs. *Methods Mol Biol.* 342: 295-312.
33. Lin S L, Chang S J E, Ying S Y. (2006b) Transgene-like animal model using intronic microRNAs. *Methods Mol Biol.* 342: 321-334.
34. Lee Y, Ahn C, Han J, Choi H, Kim J, Yim J, Lee J, Provost P, Radmark O, Kim S, Kim V N. (2003). The nuclear RNase III Drosha initiates microRNA processing. *Nature* 425: 415-419.
35. Lewin B. (2000) *Genes*, Seventh Edition, Oxford University press, page 688-690.
36. Holen et.al. (2002) *Nucleic Acid Res.* 30: 1757-1766.
37. Krol et.al. (2004) *J Biol. Chem.* 279: 42230-42239.
38. Rose A. B. (2002) *RNA* 8: 1444-1451.
39. Stoutjesdijk et. al. (2002) *Plant Physiol.* 129: 1723-1730.
40. Jin et al. (2004) *Nat Cell Biol.* 6: 1048-1053.
41. U.S. Pat. No. 7,268,108 to Pinel.
42. U.S. Pat. No. 6,852,699 to Schonrock.
43. U.S. Pat. No. 7,019,029 to Perricone.
44. U.S. Pat. No. 6,838,481 to Kim.
45. U.S. Pat. No. 6,998,130 and 7,025,977 to Wortzman.
46. U.S. Pat. No. 7,250,157 to Brown.
47. U.S. Pat. No. 6,710,076 to Ancira.
48. U.S. Pat. No. 6,514,506 to Mammone.
49. U.S. Pat. No. 7,192,617 to Nagamine.
50. U.S. Pat. No. 7,125,572 to Lee.
51. U.S. Pat. No. 6,521,267 to Steck.
52. U.S. Pat. No. 7,105,184 to Pauly.
53. U.S. Pat. No. 6,994,874, 7,060,304, and 7,247,321 to Leverett.
54. U.S. Pat. No. 7,025,957, 7,029,709, and 7,097,866 to Arquette.
55. U.S. Pat. No. 6,649,150 and 6,969,509 to Chaudhuri.
56. U.S. Pat. No. 4,289,850 to Robinson.
57. U.S. Pat. No. 6,159,714 to Lau.

SEQUENCE LISTING (1) GENERAL INFORMATION:
  (iii) NUMBER OF SEQUENCES: 25
(2) INFORMATION FOR SEQ ID NO: 1:
  (i) SEQUENCE CHARACTERISTICS:
    (A) LENGTH: 12base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO: 1: GCTAAGCCAG GC
(2) INFORMATION FOR SEQ ID NO:2:
  (i) SEQUENCE CHARACTERISTICS:
    (A) LENGTH: 12 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO:2: GCCTGGCTTA GC
(2) INFORMATION FOR SEQ ID NO:3:
  (i) SEQUENCE CHARACTERISTICS:
    (A) LENGTH: 8 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO:3: GTAAGAGK
(2) INFORMATION FOR SEQ ID NO:4:
  (i) SEQUENCE CHARACTERISTICS:
    (A) LENGTH: 10 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO:4: GWKSCYRCAG
(2) INFORMATION FOR SEQ ID NO:5:
  (i) SEQUENCE CHARACTERISTICS:
    (A) LENGTH: 7 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO:5: TACTWAY
(2) INFORMATION FOR SEQ ID NO:6:
  (i) SEQUENCE CHARACTERISTICS:
    (A) LENGTH: 17 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (iv) ANTI-SENSE: NO
  (xi) SEQUENCE DESCRIPTION: SEQ ID NO:6: TYTYCTTTTT TTTTTTS
(2) INFORMATION FOR SEQ ID NO:7:
  (i) SEQUENCE CHARACTERISTICS:
    (A) LENGTH: 19 base pairs
    (B) TYPE: nucleic acid (C) STRANDEDNESS: single
(D) TOPOLOGY: linear
(ii) MOLECULE TYPE: other nucleic acid
  (A) DESCRIPTION: /desc="synthetic"
(iii) HYPOTHETICAL: NO
(iv) ANTI-SENSE: NO
(xi) SEQUENCE DESCRIPTION: SEQ ID NO:7: TCTCTCTCTC TCTCNCTAG ,
(2) INFORMATION FOR SEQ ID NO:8:
  (i) SEQUENCE CHARACTERISTICS:
    (A) LENGTH: 78 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (xi) SEQUENCE DESCRIPTION: SEQ ID NO:8: GTCCGATCGT CGCCCTACTC TATTGCCTAA GCCGCTAAGC CAGGCGGCTT AGGCAATAGA GTAGGGCCGA CGCGTCAT
(2) INFORMATION FOR SEQ ID NO:9:
  (i) SEQUENCE CHARACTERISTICS:
    (A) LENGTH: 22 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (xi) SEQUENCE DESCRIPTION: SEQ ID NO:9: GCCCTACTCT ATTGCCTAAG CC
(2) INFORMATION FOR SEQ ID NO: 10:
  (i) SEQUENCE CHARACTERISTICS:
    (A) LENGTH: 78 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: NO
  (xi) SEQUENCE DESCRIPTION: SEQ ID NO:10: GTCCGATCGT CAGCTAGACA GTCAGGGTTT GAAGCTAAGC CAGGCTTCAA ACCCTGACTG TCTAGCTCGA CGCGTCAT
(2) INFORMATION FOR SEQ ID NO: 11:
  (i) SEQUENCE CHARACTERISTICS:
    (A) LENGTH: 22 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (xi) SEQUENCE DESCRIPTION: SEQ ID NO:11: AGCTAGACAG TCAGGGTTTG AA
(2) INFORMATION FOR SEQ ID NO: 12:
  (i) SEQUENCE CHARACTERISTICS:
    (A) LENGTH: 42 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: NO
  (xi) SEQUENCE DESCRIPTION: SEQ ID NO: 12: GTAAGAGGAT CCGATCGCAG GAGCGCACCA TCTTCTTCAA GA
(2) INFORMATION FOR SEQ ID NO: 13:
  (i) SEQUENCE CHARACTERISTICS:
    (A) LENGTH: 46 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: YES
  (xi) SEQUENCE DESCRIPTION: SEQ ID NO: 13: CGCGTCTTGA AGAAGATGGT GCGCTCCTGC GATCGGATCC TCTTAC
(2) INFORMATION FOR SEQ ID NO: 14:
  (i) SEQUENCE CHARACTERISTICS:
    (A) LENGTH: 42 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: NO
  (xi) SEQUENCE DESCRIPTION: SEQ ID NO: 14: GTAAGAGGAT CCGATCGCTT GAAGAAGATG GTGCGCTCCT GA
(2) INFORMATION FOR SEQ ID NO: 15:
  (i) SEQUENCE CHARACTERISTICS:
    (A) LENGTH: 46 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: YES
  (xi) SEQUENCE DESCRIPTION: SEQ ID NO: 15: CGCGTCAGGA GCGCACCATC TTCTTCAAGC GATCGGATCC TCTTAC
(2) INFORMATION FOR SEQ ID NO: 16:
  (i) SEQUENCE CHARACTERISTICS:
    (A) LENGTH: 70 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: NO
  (xi) SEQUENCE DESCRIPTION: SEQ ID NO: 16: GTAAGAGGAT CCGATCGCAG GAGCGCACCA TCTTCTTCAA GTTAACTTGA AGAAGATGGT GCGCTCCTGA
(2) INFORMATION FOR SEQ ID NO: 17:
  (i) SEQUENCE CHARACTERISTICS:
    (A) LENGTH: 74 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: YES (xi) SEQUENCE DESCRIPTION: SEQ ID NO: 17:
CGCGTCAGGA GCGCACCATC TTCTTCAAGT
TAACTTGAAG AAGATGGTGC GCTCCTGCGA
TCGGATCCTC TTAC (2) INFORMATION FOR SEQ ID NO: 18:
  (i) SEQUENCE CHARACTERISTICS:
    (A) LENGTH: 47 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: NO
  (xi) SEQUENCE DESCRIPTION: SEQ ID NO:18:
CGCGTTACTA ACTGGTACCT CTTCTTTTTT
TTTTTGATAT CCTGCAG (2) INFORMATION FOR SEQ ID NO: 19:
  (i) SEQUENCE CHARACTERISTICS:
    (A) LENGTH: 45 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: YES
  (xi) SEQUENCE DESCRIPTION: SEQ ID NO:19: GTC-
CTGCAGG ATATCAAAAA AAAAAGAAGA
GGTACCAGTT AGTAA 45

(2) INFORMATION FOR SEQ ID NO:20:
  (i) SEQUENCE CHARACTERISTICS:
    (A) LENGTH: 689 base pairs
    (B) TYPE: nucleic acid
    (C) STRANDEDNESS: double
    (D) TOPOLOGY: linear
  (ii) MOLECULE TYPE: cDNA to mRNA
    (A) DESCRIPTION: /desc="mutated red fluorescin gene by adding an aspartate (Asp) codon at the 69th amino acid of a HcRed1chromoprotein gene from *Heteractis crispa*"
  (iii) HYPOTHETICAL: NO
  (iv) ANTI-SENSE: NO
  (xi) SEQUENCE DESCRIPTION: SEQ ID NO:20: ATG-
GTGAGCG GCCTGCTGAA GGAGAGTATG
CGCATCAAGA TGTACATGGA GGGCACCGTG
AACGGCCACT ACTTCAAGTG CGAGGGCGAG
GGCGACGGCA ACCCCTTCGC CGGCACCCAG
AGCATGAGAA TCCACGTGAC CGAGGGCGCC
CCCCTGCCCT TCGCCTTCGA CATCCTGGCC
CCCTGCTGCG AGTACGGCAG CAGGACGACC
TTCGTGCACC ACACCGCCGA GATCCCCGAC
TTCTTCAAGC AGAGCTTCCC CGAGGGCTTC
ACCTGGGAGA GAACCACCAC CTACGAGGAC
GGCGGCATCC TGACCGCCCA CCAGGACACC
AGCCTGGAGG GCAACTGCCT GATCTACAAG
GTGAAGGTGC ACGGCACCAA CTTCCCCGCC
GACGGCCCCG TGATGAAGAA CAAGAGCGGC
GGCTGGGAGC CCAGCACCGA GGTGGTGTAC
CCCGAGAACG GCGTGCTGTG CGGCCGGAAC
GTGATGGCCC TGAAGGTGGG CGACCGGCAC
CTGATCTGCC ACCACTACAC CAGCTACCGG
AGCAAGAAGG CCGTGCGCGC CCTGACCATG
CCCGGCTTCC ACTTCACCGA CATCCGGCTC
CAGATGCTGC GGAAGAAGAA GGACGAGTAC
TTCGAGCTGT ACGAGGCCAG CGTGGCCCGG
TACAGCGACC TGCCCGAGAA GGCCAACTG (vi) ORIGINAL SOURCE: reef coral
    (A) ORGANISM: *Heteractis* spp.
    (B) STRAIN: crispa (2) INFORMATION FOR SEQ ID NO:21:
  (i) SEQUENCE CHARACTERISTICS:
    (A) LENGTH: 27 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic "
  (iii) HYPOTHETICAL: YES
  (iv) ANTI-SENSE: NO
  (xi) SEQUENCE DESCRIPTION: SEQ ID NO:21: CTC-
GAGCATG GTGAGCGGCC TGCTGAA (2) INFORMATION FOR SEQ ID NO:22:
  (i) SEQUENCE CHARACTERISTICS:
    (A) LENGTH: 27 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (iv) ANTI-SENSE: YES
  (xi) SEQUENCE DESCRIPTION: SEQ ID NO:22:
TCTAGAAGTT GGCCTTCTCG GGCAGGT (2) INFORMATION FOR SEQ ID NO:23:
  (i) SEQUENCE CHARACTERISTICS:
    (A) LENGTH: 78 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (xi) SEQUENCE DESCRIPTION: SEQ ID NO:23:
ATGACGCGTC GGCCCTACTC TATTGCCTAA
GCCGCCTGGC TTAGCGGCTT AGGCAATAGA
GTAGGGCGAC GATCGGAC (2) INFORMATION FOR SEQ ID NO:24:
  (i) SEQUENCE CHARACTERISTICS:
    (A) LENGTH: 78 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: YES
  (xi) SEQUENCE DESCRIPTION: SEQ ID NO:24:
ATGACGCGTC GAGCTAGACA GTCAGGGTTT
GAAGCCTGGC TTAGCTTCAA ACCCTGACTG
TCTAGCTGAC GATCGGAC (2) INFORMATION FOR SEQ ID NO:25:
  (i) SEQUENCE CHARACTERISTICS:
    (A) LENGTH: 117 base pairs
    (B) TYPE: nucleic acid
    (C) STRANDEDNESS: single
    (D) TOPOLOGY: linear
  (ii) MOLECULE TYPE: other nucleic acid
    (A) DESCRIPTION: /desc="synthetic"
  (iii) HYPOTHETICAL: NO
  (xi) SEQUENCE DESCRIPTION: SEQ ID NO:25: GTC-
CGATCGT CUCGACUCUG GGUUUGAACC
AAAGCUCGAC UCAUGGUUUG AACCAUUACU
UAAUUCGUGG UUUGAACCAU CACUCGACUC
CUGGUUCGAA CCAUCCGACG CGTCAT

SEQUENCE LISTING

<160> NUMBER OF SEQ ID NOS: 33

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1
gctaagccag gc                                                            12

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 2
gcctggctta gc                                                            12

<210> SEQ ID NO 3
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 3 gtaagagk                                                                  8

<210> SEQ ID NO 4
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 4 gwkscyrcag                                                               10

<210> SEQ ID NO 5
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 5 tactway                                                                   7

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
tytycttttt tttttts                                                       17

<210> SEQ ID NO 7
<211> LENGTH: 19
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: n is a, c, g, or t

<400> SEQUENCE: 7
tctctctctc tctcnctag                                              19

<210> SEQ ID NO 8
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 8
gtccgatcgt cgccctactc tattgcctaa gccgctaagc caggcggctt aggcaataga      60
gtagggccga cgcgtcat                                               78

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
gccctactct attgcctaag cc                                          22

<210> SEQ ID NO 10
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 10
gtccgatcgt cagctagaca gtcagggttt gaagctaagc caggcttcaa accctgactg      60
tctagctcga cgcgtcat                                               78

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
agctagacag tcagggtttg aa                                          22

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 12
gtaagaggat ccgatcgcag gagcgcacca tcttcttcaa ga                    42

<210> SEQ ID NO 13
<211> LENGTH: 46
<212> TYPE: DNA
```

<213> ORGANISM: Artificial Sequence
<220> FEATURE:
<223> OTHER INFORMATION: Synthetic oligonucleotide

<400> SEQUENCE: 13
cgcgtcttga agaagatggt gcgctcctgc gatcggatcc tcttac         46

<210> SEQ ID NO 14
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 14
gtaagaggat ccgatcgctt gaagaagatg gtgcgctcct ga         42

<210> SEQ ID NO 15
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 15
cgcgtcagga gcgcaccatc ttcttcaagc gatcggatcc tcttac         46

<210> SEQ ID NO 16
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 16
gtaagaggat ccgatcgcag gagcgcacca tcttcttcaa gttaacttga agaagatggt         60
gcgctcctga         70

<210> SEQ ID NO 17
<211> LENGTH: 74
<212> TYPE: DNA
<213> ORGANISM: Artificial Sequence
<220> FEATURE:
<223> OTHER INFORMATION: Synthetic oligonucleotide

<400> SEQUENCE: 17
cgcgtcagga gcgcaccatc ttcttcaagt taacttgaag aagatggtgc gctcctgcga         60
tcggatcctc ttac         74

<210> SEQ ID NO 18
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 18
cgcgttacta actggtacct cttctttttt tttttgatat cctgcag         47

<210> SEQ ID NO 19
<211> LENGTH: 45
<212> TYPE: DNA
<213> ORGANISM: Artificial Sequence
<220> FEATURE:
<223> OTHER INFORMATION: Synthetic oligonucleotide -continued

<400> SEQUENCE: 19
gtcctgcagg atatcaaaaa aaaaagaaga ggtaccagtt agtaa                    45

<210> SEQ ID NO 20
<211> LENGTH: 689
<212> TYPE: DNA
<213> ORGANISM: Heteractis spp.

<400> SEQUENCE: 20
atggtgagcg gcctgctgaa ggagagtatg cgcatcaaga tgtacatgga gggcaccgtg    60
aacggccact acttcaagtg cgagggcgag ggcgacggca ccccttcgc cggcacccag    120 agcatgagaa tccacgtgac cgagggcgcc cccctgccct tcgccttcga catcctggcc   180
ccctgctgcg agtacggcag caggacgacc ttcgtgcacc acaccgccga gatccccgac   240
ttcttcaagc agagcttccc cgagggcttc acctgggaga gaaccaccac ctacgaggac   300
ggcggcatcc tgaccgccca ccaggacacc agcctggagg gcaactgcct gatctacaag   360
gtgaaggtgc acggcaccaa cttccccgcc gacggccccg tgatgaagaa caagagcggc   420
ggctgggagc ccagcaccga ggtggtgtac cccgagaacg gcgtgctgtg cggccggaac   480
gtgatggccc tgaaggtggg cgaccggcac ctgatctgcc accactacac cagctaccgg   540
agcaagaagg ccgtgcgcgc cctgaccatg cccggcttcc acttcaccga catccggctc   600
cagatgctgc ggaagaagaa ggacgagtac ttcgagctgt acgaggccag cgtggcccgg   660
tacagcgacc tgcccgagaa ggccaactg                                     689

<210> SEQ ID NO 21
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 21
ctcgagcatg gtgagcggcc tgctgaa                                        27

<210> SEQ ID NO 22
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 22
tctagaagtt ggccttctcg ggcaggt                                        27

<210> SEQ ID NO 23
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 23
atgacgcgtc ggccctactc tattgcctaa gccgcctggc ttagcggctt aggcaataga    60
gtagggcgac gatcggac                                                  78

<210> SEQ ID NO 24
<211> LENGTH: 78
<212> TYPE: DNA

```
<213> ORGANISM: Artificial Sequence
<220> FEATURE:
<223> OTHER INFORMATION: Synthetic oligonucleotide

<400> SEQUENCE: 24
atgacgcgtc gagctagaca gtcagggttt gaagcctggc ttagcttcaa accctgactg      60
tctagctgac gatcggac                                                    78

<210> SEQ ID NO 25
<211> LENGTH: 116
<212> TYPE: DNA
<213> ORGANISM: Artificial Sequence
<220> FEATURE:
<223> OTHER INFORMATION: Synthetic mir-434-5p pre-miRNA for intronic
      insertion

<400> SEQUENCE: 25
gtccgatcgt cucgacucug gguuugaacc aaagcucgac ucaugguuug aaccauuacu      60
uaauucgugg uuugaaccau cacucgacuc cugguucgaa ccauccgacg cgtcat         116

<210> SEQ ID NO 26
<211> LENGTH: 11
<212> TYPE: RNA
<213> ORGANISM: Artificial Sequence
<220> FEATURE:
<223> OTHER INFORMATION: Synthetic short tRNA loop

<400> SEQUENCE: 26
wuccaagggg g                                                           11

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 27
gtaagaggat                                                             10

<210> SEQ ID NO 28
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 28
gatatcctgc ag                                                          12

<210> SEQ ID NO 29
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 29
aggtaagagt cgatcgacgc gttactaact ggtacctctt cttttttttt tgatatcctg      60
caggc                                                                  65

<210> SEQ ID NO 30
<211> LENGTH: 53
<212> TYPE: DNA
```

```
<213> ORGANISM: Artificial Sequence
<220> FEATURE:
<223> OTHER INFORMATION: Synthetic oligonucleotide

<400> SEQUENCE: 30
tccaggagcg caccatcttc tttagagaac taagaagatg gtgcgctcct gga          53

<210> SEQ ID NO 31
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 31
aagaagatgg tgcgctcctg gatcaagaga ttccaggagc gcaccatctt ctt          53

<210> SEQ ID NO 32
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 32
caagaagatg gtgcgctcct ggatcaagag attccaggag cgcaccatct tctt         54

<210> SEQ ID NO 33
<211> LENGTH: 63
<212> TYPE: DNA
<213> ORGANISM: Artificial Sequence
<220> FEATURE:
<223> OTHER INFORMATION: Synthetic primer

<400> SEQUENCE: 33
ggccagtgaa ttgtaatacg actcactata gggaggcggt tttttttttt tttttttttt   60
ttt                                                                 63
```

The invention claimed is:

1. An isolated nucleic acid composition for inducing microRNA mir-434-associated gene silencing effects against tyrosinase, comprising:
a SpRNAi-RGFP expression vector capable of expressing an intronic RNA molecule having a sequence which contains the sequence of SEQ.ID.NO:8, wherein the intronic RNA molecule having the sequence of SEQ.ID.NO.8 targets tyrosinase gene.

2. The isolated nucleic acid composition as defined in claim 1, wherein said intronic RNA molecule contains a sequence which contains the sequence of SEQ ID NO:9 for inducing gene silencing against tyrosinase and is processed into a mature microRNA having the sequence of SEQ.ID.NO.9.

3. The isolated nucleic acid composition as defined in claim 1, wherein said intronic RNA molecule contains a hairpin stem-loop structure.

4. The isolated nucleic acid composition as defined in claim 3, wherein said hairpin stem-loop structure contains a sequence which contains the sequence of either SEQ ID NO:1 or the sequence of SEQ ID NO:2 for inducing gene silencing against tyrosinase.

5. The isolated nucleic acid composition as defined in claim 1, which is a nucleic acid template encoding said intronic RNA molecule.

6. The isolated nucleic acid composition as defined in claim 1, further containing a 5'-donor splice site, a 3'-acceptor splice site, and a branch point motif.

7. The isolated nucleic acid composition as defined in claim 1, further containing sequences which contains the sequence of SEQ.ID.NO:3, the sequence of SEQ.ID.NO:4, and the sequence of SEQ.ID.NO:5.

8. The isolated nucleic acid composition as defined in claim 1, further containing a recombinant mir-434-5p pre-miRNA insert having the sequence of SEQ.ID.NO:25.

9. The isolated nucleic acid composition as defined in claim 1, which can be delivered into cells for expression.

10. The isolated nucleic acid composition as defined in claim 9, which can be delivered into cells by vector transfection.

11. The isolated nucleic acid composition as defined in claim 10, wherein said vector is a plasmid or its derivative.

* * * * *